United States Patent [19]

Ehrenfreund

[11] Patent Number: 4,965,389
[45] Date of Patent: Oct. 23, 1990

[54] PHENOXYPHENYLTHIOUREAS PHENOXYPHENYLISOTHIOUREAS AND PHENOXYPHENYLCARBODIIMIDES AND USE THEREOF FOR CONTROLLING PESTS

[75] Inventor: Josef Ehrenfreund, Allshwil, Switzerland

[73] Assignee: Ciba-Geigy Corporation, Ardsley, N.Y.

[21] Appl. No.: 162,536

[22] Filed: Mar. 1, 1988

[30] Foreign Application Priority Data

Mar. 10, 1987 [CH] Switzerland ............................ 878/87
Jan. 11, 1988 [CH] Switzerland ............................. 65/88

[51] Int. Cl.$^5$ ........................................... C07C 157/09
[52] U.S. Cl. ........................................ 558/04; 564/28; 564/252
[58] Field of Search ...................... 558/4; 564/28, 252; 514/475, 580

[56] References Cited

U.S. PATENT DOCUMENTS

| 4,194,008 | 3/1980 | Enders et al. | ............... 424/322 |
| 4,328,247 | 5/1982 | Drabek et al. | ............... 424/326 |
| 4,404,225 | 9/1983 | Böger et al. | ................ 424/322 |

FOREIGN PATENT DOCUMENTS

| 1234120 | 3/1988 | Canada . |
| 113247 | 7/1984 | European Pat. Off. . |
| 0296120 | 12/1988 | European Pat. Off. . |
| 3801395 | 8/1988 | Fed. Rep. of Germany . |
| 86/5781 | 10/1986 | PCT Int'l Appl. . |
| 783880 | 6/1978 | South Africa . |
| 1571970 | 7/1980 | United Kingdom . |
| 2060626 | 5/1981 | United Kingdom . |

Primary Examiner—Paul J. Killos
Attorney, Agent, or Firm—Edward McC. Roberts

[57] ABSTRACT

The invention relates to novel phenoxyphenylthioureas, phenoxyphenylisothioureas and phenoxyphenylcarbodiimides of formula I

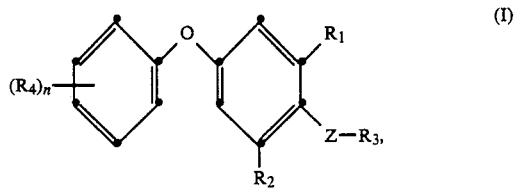

wherein
$R_1$ is $C_3$-$C_7$cycloalkyl or $C_5$-$C_6$cycloalkenyl,
$R_2$ is $C_1$-$C_6$alkyl, $C_5$-$C_6$cycloalkyl or $C_5$-$C_6$cycloalkenyl,
$R_3$ is $C_1$-$C_8$alkyl, $C_3$-$C_6$cycloalkyl, 1-cyclopropylethyl or $C_3$-$C_5$alkenyl,
$R_4$ is hydrogen, halogen, $C_1$-$C_4$alkyl, $C_1$-$C_3$alkoxy or $CF_3$,
n is an integer from 1 to 3,
Z is —NH—CS—NH—, —N=C(SR$_5$)—NH— or —N=C=N—, and
$R_5$ is $C_1$-$C_5$alkyl or allyl,
and to salts thereof, to the preparation of these compounds and to intermediates for their synthesis. The invention further relates to the use of the novel compounds in pest control and to pesticidal compositions which contain at least one compound of formula I. The preferred utility is the control of pests of animals and plants.

22 Claims, No Drawings

PHENOXYPHENYLTHIOUREAS PHENOXYPHENYLISOTHIOUREAS AND PHENOXYPHENYLCARBODIIMIDES AND USE THEREOF FOR CONTROLLING PESTS

The present invention relates to novel substituted phenoxyphenylthioureas, phenoxyphenylisothioureas and phenoxyphenylcarbodiimides, to salts thereof with organic and inorganic acids, to their preparation and to intermediates for their preparation. The invention further relates to pesticidal compositions which contain these compounds and to the use thereof in pest control.

The compounds of this invention have the formula I

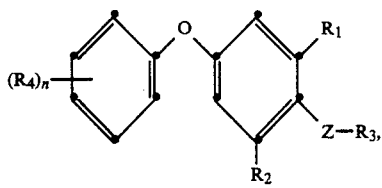

wherein
$R_1$ is $C_3$-$C_7$cycloalkyl or $C_5$-$C_6$cycloalkenyl,
$R_2$ is $C_1$-$C_6$alkyl, $C_5$-$C_6$cycloalkyl or $C_5$-$C_6$cycloalkenyl,
$R_3$ is $C_1$-$C_8$alkyl, $C_3$-$C_6$cycloalkyl, 1-cyclopropylethyl or $C_3$-$C_5$alkenyl,
$R_4$ is hydrogen, halogen, $C_1$-$C_4$alkyl, $C_1$-$C_3$alkoxy or $CF_3$,
n is an integer from 1 to 3,
Z is —NH—CS—NH—, —N=C(SR$_5$)—NH— or —N=C=N—, and
$R_5$ is $C_1$-$C_5$alkyl or allyl.

Suitable halogen substituents are fluorine and chlorine as well as bromine and iodine, with fluorine and chlorine being preferred.

Alkyl groups can be straight chain or branched. Such alkyl groups may be for example methyl, ethyl, propyl, isopropyl as well as butyl and pentyl and the isomers thereof. This definition also applies correspondingly to the alkoxy substituents.

Cycloalkyl and cycloalkenyl groups may be for example cyclopropyl, cyclobutyl, cyclopentyl, cyclopentenyl, cyclohexyl, cyclohexenyl or cycloheptyl. These groups may also be substituted by one or two $C_1$-$C_3$alkyl groups.

The alkenyl groups can be straight chain or branched and contain one or more double bonds. Examples of such alkenyl groups comprise vinyl, allyl, 1-propenyl, isopropenyl, allenyl, butenyls, butadienyls or pentenyls.

The compounds of formula I, wherein Z is —N=C(SR$_5$)—NH—, can also be in the form of acid addition salts. Acids suitable for forming such salts are organic as well as inorganic acids. Examples of such acids are: hydrochloric acid, hydrobromic acid, hydroiodic acid, nitric acid, different phosphoric acids, sulfuric acid, acetic acid, propionic acid, butyric acid, valeric acid, oxalic acid, malonic acid, succinic acid, malic acid, maleic acid, fumaric acid, lactic acid, tartaric acid, citric acid, benzoic acid, phthalic acid, cinnamic acid, phenylsulfonic acid and salicylic acid.

Compounds of formula I, wherein Z is —N=C(SR$_5$)—NH—, can be obtained in their tautomeric forms

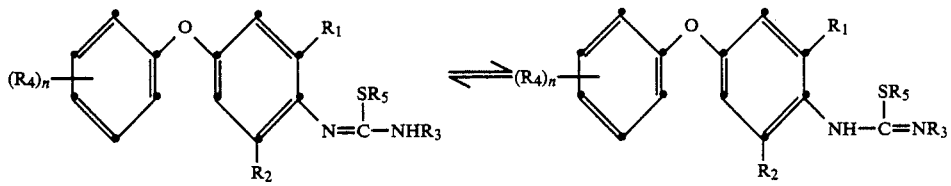

The invention encompasses the individual tautomers as well as mixtures of tautomers.

Preferred compounds of formula I are those wherein $R_1$ is $C_3$-$C_7$cycloalkyl, $R_2$ is $C_1$-$C_4$alkyl or cyclopentyl, $R_3$ is $C_1$-$C_4$alkyl or $C_3$-$C_5$cycloalkyl, $R_4$ is hydrogen, halogen or $C_1$-$C_3$alkyl, n is 1 or 1, Z is —NH—CS—NH—, —N=C(SR$_5$)—NH— or —N=C=N—, and $R_5$ is $C_1$-$C_3$alkyl.

Among this group of compounds, those compounds of formula I are preferred wherein
(a) $R_1$ is $C_5$-$C_6$cycloalkyl, $R_2$ is ethyl or isopropyl, $R_3$ is isopropyl, tert-butyl or cyclopentyl, $R_4$ is hydrogen or fluorine, n is 1 or 2, and Z is —NH—CS—NH—; or
(b) $R_1$ is $C_5$-$C_6$cycloalkyl, $R_2$ is ethyl or isopropyl, $R_3$ is isopropyl, tert-butyl or cyclopentyl, $R_4$ is hydrogen or fluorine, n is 1 or 2, Z is —N=C(SR$_5$)—NH—, and $R_5$ is methyl or ethyl; or
(c) $R_1$ is $C_5$-$C_6$cycloalkyl, $R_2$ is ethyl or isopropyl, $R_3$ is isopropyl, tert-butyl or cyclopentyl, $R_4$ is hydrogen or fluorine, n 1 or 2, and Z is —N=C=N—.

The compounds of formula I of this invention can be prepared by methods which are known per se, for example by (A) reacting an isothiocyanate of formula II

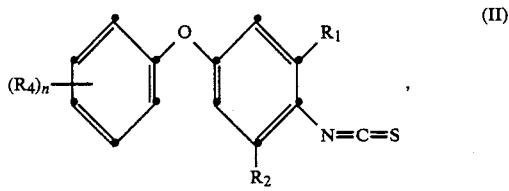

with an amine of formula II

to give the thiourea and, if desired, (B) reacting the resultant thiourea with a compound of formula IV

to give the isothiourea, or (C) converting the resultant isothiourea into the carbodiimide by removal of hydrogen sulfide. In the formulae above, $R_1$, $R_2$, $R_3$, $R_4$, $R_5$ and n have the given meanings and X is a suitable leaving group, for example a halogen atom, preferably a chlorine, bromine or iodine atom, or alkylsulfate.

Process (A) is normally carried out under normal pressure and in the presence of an organic solvent or diluent. The reaction temperature is in the range from 0° to 150° C., preferably from 10° to 70° C. Examples of suitable solvents or diluents are: ethers and ethereal compounds such as diethyl ether, dipropyl ether, dibutyl ether, dioxane, dimethoxyethane and tetrahydrofuran; N,N-dialkylated carboxamides; aliphatic, aromatic and halogenated hydrocarbons such as benzene, toluene, xylenes, chloroform, methylene chloride, carbon tetrachloride and chlorobenzine; nitriles such as acetonitrile or propionitrile; and ketones, e.g. acetone, methyl ethyl ketone, methyl isopropyl ketone, methyl isobutyl ketone and cyclohexanone.

Process (B) conveniently carried out in an inert organic solvent and under slightly elevated or normal pressure. The reaction temperature is in the range from 10° to 250° C., but is preferably the boiling temperature of the solvent employed or from 50° to 150° C. Examples of suitable solvents or diluents are: ethers and ethereal compounds such as diethyl ether, diisopropyl ether, dioxane and tetrahydrofuran; aromatic hydrocarbons such as benzene, toluene and xylenes; ketones such as acetone, methyl ethyl ketone and cyclohexanone; alcohols or dimethyl formamide.

Process (C) is conveniently carried out in an aprotic organic solvent or diluent and under normal pressure. The reaction temperature is in the range from 0° to 150° C., preferably from 10° to 50° C. Examples of suitable solvents or diluents are: ethers and ethereal compounds such as diethyl ether, dipropyl ether, dibutyl ether, dioxane, dimethoxyethane and tetrahydrofuran; N,N-dialkylated carboxamides; aliphatic, aromatic and halogenated hydrocarbons such as benzene, toluene, xylenes, chloroform, methylene chloride, carbon tetrachloride and chlorbenzine; nitriles such as acetonitrile and propionitrile; and ketones, e.g. acetone, methyl ethyl ketone, methyl isopropyl ketone, methyl isobutyl ketone and cyclohexanone. The removal of hydrogen sulfide is effected by methods which are described in the literature [T. Shibanuma, Chemistry Letters (1977), pp. 575–6; S. Kim, Tetrahedron Letters (1985), pp. 1661–1664; W. Weith, B. 6 (1873) 1398; G. Amiard, Bull. Soc. chim. 1956, 1360]. Suitable reagents for the elimination reaction are e.g. HgO, specific pyridinium salts, chloroacetates, cyanuric chloride, p-toluenesulfochloride or specific phosphate derivatives.

The isothiocyanates of formula II can be prepared by methods which are known per se, for example by thioposgenating a phenoxyaniline of formula V

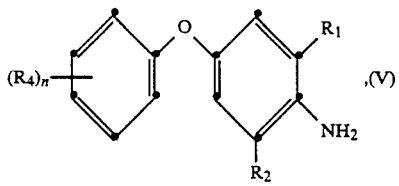

wherein $R_1$, $R_2$, $R_4$ and n are as defined for formula I.

The process for the preparation of the compounds of formula II is conveniently carried out in the presence of an organic or inorganic base such as triethylamine or calcium carbonate and in an inert solvent or diluent under normal pressure. The reaction is carried out in the temperature range from 0° to 100° C., preferably at the boiling temperature of the solvent or diluent employed, or in the range from 20° to 80° C. Suitable solvents and diluents are, for example, ethers or ethereal compounds such as diethyl ether, diisopropyl ether, dioxane or tetrahydrofuran; aromatic hydrocarbons such as benzene, toluene or xylenes; ketones such as acetone, methyl ethyl ketone or cyclohexanone; or chlorinated hydrocarbons such as dichloromethane. The reaction can also be carried out in the presence of water in a two-phase system.

The phenoxyanilines of formula V can be prepared by methods which are known per se, for example by reacting an aniline of formula VI

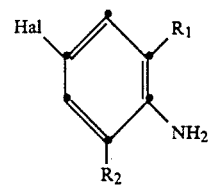

with a phenol of formula VII

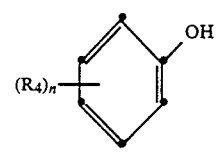

in which formulae (VI) and (VII) above $R_1$, $R_2$, $R_4$ and n are as defined for formula I and Hal is halogen, preferably chlorine or bromine.

The process for the preparation of compounds of formula V is conveniently carried out in the presence of an organic or, preferably, inorganic base, for example an alkali metal hydroxide or alkali metal carbonate, and in an inert, preferably polar, solvent or diluent and under normal pressure. The process is carried out in the temperature range from 0° to 200° C., preferably at the boiling point of the solvent or diluent employed, or in the range from 50° to 170° C. It can be advantageous to add a heavy metal catalyst, for example copper powder or basic copper(II) carbonate. Examples of suitable solvents and diluents are amides such as dimethyl formamide, dimethyl sulfoxide, N-methylpyrrolidone and other aprotic dipolar solvents.

The compounds of formulae II and V are novel and likewise constitute an object of the present invention. The compounds of formulae III, IV, VI (q.v. German Offenlegungsschrift 27 27 529; Synth. Communications, Vol. 16/809, 1986) on the other hand are known or can be prepared by methods which are known per se.

German Offenlegungsschrift specification Nos. 26 39 748, 27 02 235, 27 27 416, 27 27 529 and 27 30 620 disclose phenylthioureas and phenylisothioureas which may be substituted in 2,6-position of the N-phenyl ring by cycloalkyl groups, but contain no phenoxy group. German Offenlegungsschrift No. 30 34 015 and published European patent application Nos. 025 010 and 175 649 disclose phenoxyphenylcarbodiimides, phenoxyphenylthioureas and phenoxyphenylisothioureas which do not contain any phenoxy groups in positions 2 and 6 of the N-phenyl ring. All these known compounds are pesticidally active, but are not well tolerated by plants.

Surprisingly, it has been found that the compounds of formula I of this invention are valuable pesticides while being well tolerated by warm-blooded animals and plants. The compounds of formula I are therefor suitable e.g. for controlling pests of animals and plants. Such pests belong principally to the phylum of Arthropoda, such as in particular insects of the orders Lepidoptera, Coleoptera, Homoptera, Heteroptera, Diptera, thysanoptera, Orthoptera, Anoplura, Siphonaptera, Mallophaga, Thysanura, Isoptera, Psocoptera or Hymenoptera and arachnids of the order Acarina, e.g. mites and ticks. Every development stage of the pests can be controlled, i.e. the adults, pupae and nymphs, and also in particular the larvae and eggs. It is thus possible to control effectively in particular larvae and eggs of phytopathogenic insect pests and mites in crops of ornamentals and useful plants, e.g. in fruit and vegetable crops, and especially in cotton crops. If compounds of formula I are ingested by imagines, then a direct kill of the pests or a reduced oviposition and/or hatching rate can be observed. This last activity can be observed in particular in Coleoptera. In the control of pests that are parasites of animals, in particular of domestic animals and productive livestock, the chief pests are ectoparasites, such as mites and ticks and Diptera, for example *Lucilia sericata*.

The good pesticidal activity of the compounds of formula I corresponds to a morality of at least 50-60% of the above pests.

The activity of the compounds of formula I and of the compositions containing them can be substantially broadened and adapted to prevailing circumstances by addition of other insecticides and/or acaricides. Examples of suitable additives include: organophosphorus compounds, nitrophenols and derivatives thereof, formamidines, ureas, carbamates, pyrethroids, chlorinated hydrocarbons, and Bacillus thuringiensis preparations.

The compounds of formula I are used in unmodified form, or preferably together with the inert, agriculturally acceptable adjuvants conventionally employed in the art of formulation, and can therefore be formulated in known manner to emulsifiable concentrates, directly sprayable or dilutable solutions, dilute emulsions, wettable powders, soluble powders, dusts granulates, and also encapsulations in e.g. polymer substances. As with the compositions, the methods of application such as spraying, atomishing, dusting, scattering or pouring, are chosen in accordance with the intended objectives and the prevailing circumstances.

The formulations, i.e. the compositions, preparations or mixtures containing the compound (active ingredient) of formula I or combinations thereof with other insecticides or acaricides, and, where appropriate, a solid or liquid adjuvant, are prepared in known manner, e.g. by homogenously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated absorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I to be formulated, or of combinations thereof with other insecticides or acaricides, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate, or o a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonatres are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, castor oil thioxilate, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$-$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltryltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp., Ridgewood, New Jersey, 1979; Dr. Helmut Stache, "Tensid Taschenbuch" (handbook of Surfactants), Carl Hanser Verlag, Munich/Vienna, 1981.

The pesticidal compositions usually contain 0.1 to 99%, preferably 0.1 to 95%, of a compound of formula I or a combination thereof with other insecticides or acaricides, 1 to 99% of a solid or liquid adjuvant, and 0 to 25%, preferably 0.1 to 20%, of a surfactant.

Whereas commercial products are preferably formulated as concentrates, the end user will normally employ diluted formulations of substantially lower concentration.

The compositions may also contain further ingredients, such as stabilisers, antifoams, viscosity regulators, binders, tackifiers as well as fertilisers or other active ingredients for obtaining special effects.

EXAMPLE 1: Preparation 1.1. Intermediates
1.1.1. 4-Phenoxyanilines 1.1.1.1. 2-Cyclohexyl-4-phenoxy-6-isopropylaniline 5.7 g of phenol are dissolved in 30 ml of toluene and to the solution are added 0.8 g of ground potassium carbonate and 6.8 g of a 50% aqueous solution of potassium hydroxide. The water of reaction is removed from the system over 5 hours and then the toluene is removed by distillation. To the residue are added 30 ml of dimethyl formamide and 0.25 g of basic copper carbonate, whereupon solvent is distilled off until the temperature in the reactor has reached 140° C. Then 11.9 g of 2-cyclohexyl-4-bromo-6-isopropylaniline are added dropwise to the reaction mixture at this temperature and the batch is stirred for 16 hours while maintaining the same temperature. The solvent is subsequently removed by vacuum distillation and the residue is diluted with ether and filtered. The organic phase is washed twice with 10% aqueous sodium hydroxide solution and water and dried over sodium sulfate. The solvent is removed under vacuum, affording the title compound of formula

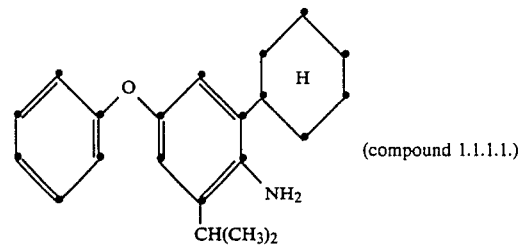

(compound 1.1.1.1.)

as a dark brown solid which melts at 108°–110° C. after recrystallisation from hexane.

The following compounds are prepared in analogous manner.

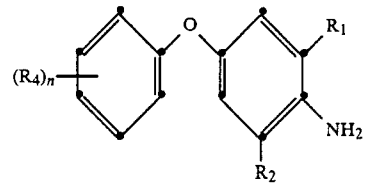

| Compound | n | $R_1$ | $R_2$ | $R_4$ | Physical data |
|---|---|---|---|---|---|
| 1.1.1.2. | 1 | cyclohexyl | $C_2H_5$ | H | nmr (CDCl$_3$): δ = 1.3 (t,3); 1.4–2.2 (m,10); 2.5 (m,3); 3.6 (broad, 2; exchangeable with D$_2$O); 6.6–7.4 (m,7); |
| 1.1.1.3. | 1 | cyclopentyl | CH(CH$_3$)$_2$ | H | nmr (CDCl$_3$): δ = 1.22 (d,6); 1.4–2.2 (m,8); 2.95 (m,2); 3.55 (broad, 2; exchangeable with D$_2$O); |
| 1.1.1.4. | 1 | cyclopentyl | $C_2H_5$ | H | nmr (CDCl$_3$): δ = 1.25 (t,3); 1.4–2.25 (m,8); 2.55 (q,2); 3.05 (m,1); 3.6 (broad s,2; exchangeable with D$_2$O); 6.65–7.1 (m,5); 7.15–7.4 (m,2); 6.7–7.4 (m,7); |
| 1.1.1.5. | 1 | cyclopentyl | CH(CH$_3$)$_2$ | 4-F | $n_D^{23}$: 1.5760 |
| 1.1.1.6. | 1 | cyclopentyl | $C_2H_5$ | 4-F | $n_D^{21}$: 1.5822 |
| 1.1.1.7. | 1 | cyclopentyl | $C_2H_5$ | 3-F | nmr (CDCl$_3$): δ = 1.28 (t,3); 1.4–2.3 (m,8); 2.55 (q,2); 3.05 (m,1); 3.65 (broad s,2; exchangeable with D$_2$O); 6.5–6.9 (m,5); 7.2 (m,1); |
| 1.1.1.8. | 1 | cyclopentyl | CH(CH$_3$)$_2$ | 3-F | nmr (CDCl$_3$): δ = 1.25 (d,6); 1.4–2.3 (m,8); 2.7–3.25 (m,2); 3.8 (broad s,2; exchangeable with D$_2$O); 6.5–6.9 (m,5);7.15 (m,1); |
| 1.1.1.9. | 1 | cyclopentyl | CH(CH$_3$)$_2$ | 2-F | m.p. 71–73° C. |
| 1.1.1.10. | 1 | cyclopentyl | $C_2H_5$ | 2-F | $n_D^{22}$: 1.5800 |
| 1.1.1.11. | 1 | cyclopentyl | cyclopentyl | H | $n_D^{25}$: 1.5938 |
| 1.1.1.12. | 2 | cyclopentyl | CH(CH$_3$)$_2$ | 3-F,5-F | $n_D^{26}$: 1.5596 |
| 1.1.1.13. | 2 | cyclopentyl | CH(CH$_3$)$_2$ | 2-F,4-F | nmr (CDCl$_3$): δ = 1.22 (d,6); 1.4–2.2 (m,8); |

| Compound | n | $R_1$ | $R_2$ | $R_4$ | Physical data |
|---|---|---|---|---|---|
| | | | | | 2.75–3.2 (m,2); 3.6 (broad s, exchangeable with $D_2O$); 6.5–7.2 (m,3); 6.7 (s,2). |
| | 1 | cyclopentyl | $CH(CH_3)_2$ | 4-$C(CH_3)_3$ | |
| | 1 | cyclopentyl | $CH(CH_3)_2$ | 4-Cl | |
| | 1 | cyclopentyl | $CH(CH_3)_2$ | 3-$CF_3$ | |

1.1.2. Phenylisothiocyanates

1.1.2.1. 2-Cyclohexyl-4-phenoxy-6-isopropyl-phenylisothiocyanate

A solution of 7.0 g of 2-cyclohexyl-4-phenoxy-6-isopropylaniline in 20 ml of dichloromethane is added dropwise, with efficient stirring, to 3.1 g of thiophosgene, 40 ml of dichloromethane, 20 ml of water and 5.0 g of ground calcium carbonate. The reaction mixture is stirred for 5 hours under reflux, then cooled and filtered over kieselguhr. The organic phase is separated, washed with water, dried over sodium sulfate and the solvent is removed under vacuum. The title compound of formula

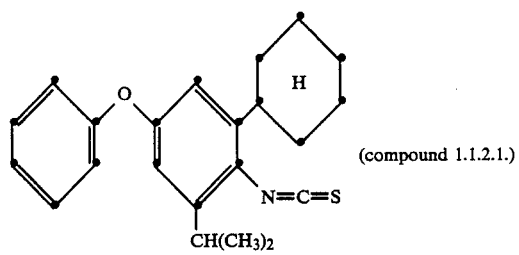

(compound 1.1.2.1.)

is obtained in the form of yellow crystals which melt at 58°–60° C.

The following compounds are prepared in analogous manner:

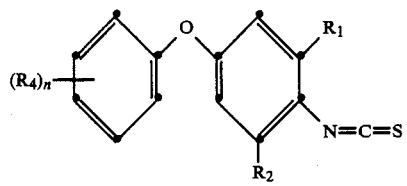

| Compound | n | $R_1$ | $R_2$ | $R_4$ | Phys. data |
|---|---|---|---|---|---|
| 1.1.2.2. | 1 | cyclohexyl | $C_2H_5$ | H | yellow oil |
| 1.1.2.3. | 1 | cyclopentyl | $CH(CH_3)_2$ | H | yellow oil |
| 1.1.2.4. | 1 | cyclopentyl | $C_2H_5$ | H | yellow oil |
| 1.1.2.5. | 1 | cyclopentyl | $CH(CH_3)_2$ | 4-F | $n_D^{24}$: 1.6080 |
| 1.1.2.6. | 1 | cyclopentyl | $C_2H_5$ | 4-F | $n_D^{22}$: 1.6118 |
| 1.1.2.7. | 1 | cyclopentyl | $C_2H_5$ | 3-F | $n_D^{21}$: 1.6142 |
| 1.1.2.8. | 1 | cyclopentyl | $CH(CH_3)_2$ | 3-F | $n_D^{22}$: 1.6100 |
| 1.1.2.9. | 1 | cyclopentyl | $CH(CH_3)_2$ | 2-F | $n_D^{24}$: 1.6075 |
| 1.1.2.10. | 1 | cyclopentyl | $C_2H_5$ | 2-F | $n_D^{23}$: 1.6148 |
| 1.1.2.11. | 1 | cyclopentyl | cyclopentyl | H | $n_D^{22}$: 1.6265 |
| 1.1.2.12. | 2 | cyclopentyl | $CH(CH_3)_2$ | 3-F,5-F | $n_D^{26.5}$: 1.5991 |
| 1.1.2.13. | 2 | cyclopentyl | $CH(CH_3)_2$ | 2-F,4-F | $n_D^{23}$: 1.5959 |
| | 1 | cyclopentyl | $CH(CH_3)_2$ | 4-$C(CH_3)_3$ | |
| | 1 | cyclopentyl | $CH(CH_3)_2$ | 4-Cl | |
| | 1 | cyclopentyl | $CH(CH_3)_2$ | 3-$CF_3$ | |

1.2. Final products

1.2.1. Phenoxyphenylthioureas

1.2.1.1. N-(2-Cyclohexyl-4-phenoxy-6-isopropyl)phenyl-N'-tert-butylthiourea 7.3 g of 2-cyclohexyl-4-phenoxy-6-isopropylphenylisothiourea are dissolved in 15 ml of tetrahydrofuran and to the solution are added 3.3 g of tert-butylamine. The reaction mixture is allowed to stand for 20 hours at room temperature and then extracted 3 times with hexane. The hexane extracts are dried over sodium sulfate and finally the hexane is removed by distillation. The title compound of formula

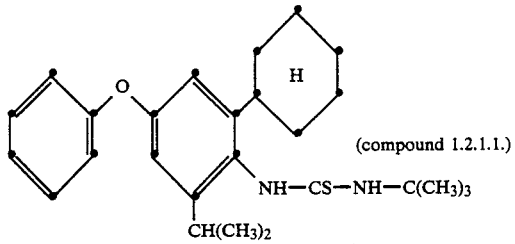

(compound 1.2.1.1.)

is recrystallised from hexane and melts at 134°–136° C.

The following compounds are prepared in analogous manner:

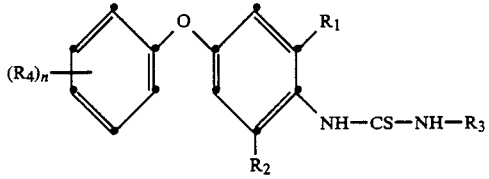

| Compound | n | $R_1$ | $R_2$ | $R_3$ | $R_4$ | Phys. data |
|---|---|---|---|---|---|---|
| 1.2.1.2. | 1 | cyclohexyl | $C_2H_5$ | $C(CH_3)_3$ | H | m.p. 116–119° C. |
| 1.2.1.3. | 1 | cyclopentyl | $CH(CH_3)_2$ | $C(CH_3)_3$ | H | m.p. 125.5–126.5° C. |
| 1.2.1.4. | 1 | cyclopentyl | $CH(CH_3)_2$ | $CH(CH_3)_2$ | H | m.p. 137.5–139° C. |
| 1.2.1.5. | 1 | cyclopentyl | $C_2H_5$ | $C(CH_3)_3$ | H | m.p. 109.5–110.5° C. |
| 1.2.1.6. | 1 | cyclopentyl | $C_2H_5$ | $CH(CH_3)_2$ | H | m.p. 146.5–147.5° C. |
| 1.2.1.7. | 1 | cyclopentyl | $CH(CH_3)_2$ | $C(CH_3)_3$ | 4-F | amorphous powder |
| 1.2.1.8. | 1 | cyclopentyl | $CH(CH_3)_2$ | $CH(CH_3)_2$ | 4-F | amorphous powder |
| 1.2.1.9. | 1 | cyclopentyl | $CH(CH_3)_2$ | $C(CH_3)_3$ | 3-F | m.p. 117–118° C. |
| 1.2.1.10. | 1 | cyclopentyl | $CH(CH_3)_2$ | $CH(CH_3)_2$ | 3-F | m.p. 104–105.5° C. |

-continued

| Compound | n | R₁ | R₂ | R₃ | R₄ | Phys. data |
|---|---|---|---|---|---|---|
| 1.2.1.11 | 1 | cyclopentyl | $C_2H_5$ | $C(CH_3)_3$ | 3-F | m.p. 98–100° C. |
| 1.2.1.12. | 1 | cyclopentyl | $C_2H_5$ | $CH(CH_3)_2$ | 3-F | m.p. 111–113° C. |
| 1.2.1.13. | 1 | cyclopentyl | $CH(CH_3)_2$ | $C(CH_3)_3$ | 2-F | m.p. 96–98° C. |
| 1.2.1.14. | 1 | cyclopentyl | $CH(CH_3)_2$ | $CH(CH_3)_2$ | 2-F | m.p. 168.5–170° C. |
| 1.2.1.15. | 1 | cyclopentyl | $C_2H_5$ | $C(CH_3)_3$ | 2-F | m.p. 129.5–131° C. |
| 1.2.1.16. | 1 | cyclopentyl | cyclopentyl | $C(CH_3)_3$ | H | m.p. 133.5–135.5° C. |
| 1.2.1.17. | 1 | cyclopentyl | cyclopentyl | $CH(CH_3)_2$ | H | m.p. 174.5–177° C. |
| 1.2.1.18. | 2 | cyclopentyl | $CH(CH_3)_2$ | $CH(CH_3)_2$ | 3-F, 5-F | m.p. 132–134° C. |
| 1.2.1.19. | 1 | cyclopentyl | $CH(CH_3)_2$ | cyclopentyl | H | m.p. 157–158.5° C. |
| 1.2.1.20. | 2 | cyclopentyl | $CH(CH_3)_2$ | $CH(CH_3)_2$ | 2-F, 4-F | m.p. 118–120° C. |
| 1.2.1.21. | 2 | cyclopentyl | $CH(CH_3)_2$ | $C(CH_3)_3$ | 2-F, 4-F | m.p. 104.5–106° C. |
| 1.2.1.22. | 1 | cyclopentyl | $CH(CH_3)_2$ | $CH(CH_3)C_2H_5$ | H | m.p. 149–150° C. |
| 1.2.1.23. | 1 | cyclopentyl | $CH(CH_3)_2$ | $CH(CH_3)CH(CH_3)_2$ | H | m.p. 151–152° C. |
| 1.2.1.24. | 1 | cyclopentyl | $CH(CH_3)_2$ | $CH(CH_3)$cyclopropyl | H | m.p. 147–148° C. |
| 1.2.1.25. | 1 | cyclopentyl | $CH(CH_3)_2$ | $C(CH_3)_2C_2H_5$ | H | $n_D^{25}$:1.5672 |
| 1.2.1.26. | 1 | cyclopentyl | $CH_3$ | $C(CH_3)_3$ | H | m.p. 108–109° C. |
| 1.2.1.27. | 1 | cyclopentyl | $CH_3$ | $CH(CH_3)_2$ | H | m.p. 129.5–130.5° C. |
|  | 1 | cyclopentyl | $C_2H_5$ | $C(CH_3)_3$ | 4-F |  |
|  | 1 | cyclopentyl | $C_2H_5$ | $CH(CH_3)_2$ | 4-F |  |
|  | 1 | cyclopentyl | $C_2H_5$ | $CH(CH_3)_2$ | 2-F |  |
|  | 1 | cyclopentyl | $CH(CH_3)_2$ | $C(CH_3)_3$ | $C(CH_3)_3$ |  |
|  | 1 | cyclopentyl | $CH(CH_3)_2$ | $CH(CH_3)_2$ | $C(CH_3)_3$ |  |
|  | 1 | cyclopentyl | $CH(CH_3)_2$ | $C(CH_3)_3$ | 4-Cl |  |
|  | 1 | cyclopentyl | $CH(CH_3)_2$ | $CH(CH_3)_2$ | 4-Cl |  |
|  | 1 | cyclopentyl | $CH(CH_3)_2$ | $C(CH_3)_3$ | 3-$CF_3$ |  |
|  | 1 | cyclopentyl | $CH(CH_3)_2$ | $CH(CH_3)_2$ | 3-$CF_3$ |  |
|  | 2 | cyclopentyl | $CH(CH_3)_2$ | $C(CH_3)_3$ | 3-F, 5-F |  |

1.2.2. Phenoxyphenylisothioureas 1.2.2.1. N-(2-Cyclohexyl-4-phenoxy-6-isopropyl)phenyl-N'-tert-butyl-S-methylisothiourea 2.6 g of N-(2-cyclohexyl-4-phenoxy-6-isopropyl)phenyl-N'-tert-butylthiourea are charged to 35 ml of ethanol, then 1.3 g of methyl iodide are added at room temperature and the reaction mixture is stirred for 6 hours at room temperature. The reaction solution is then cooled, poured into 500 ml of water and extracted 3 times with methylene chloride. The organic phases are washed 3 times with 5% aqueous sodium carbonate solution and with water, dried over sodium sulfate, and finally the solvent is removed by evaporation. The residue is chromatographed over silica gel with a 4:1 mixture of hexane/ether as eluant. The title compound of formula

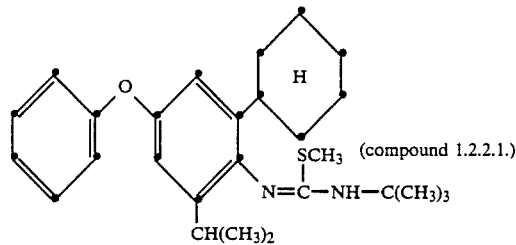

(compound 1.2.2.1.)

is obtained in the form of colourless crystals which melt at 91°–99° C.

The HI salt of N-(2-cyclopentyl-4-phenoxy-6-isopropyl)phenyl-N'-isopropyl-S-methylisothiourea (compound 1.2.2.3.) is prepared as follows: 5.0 g of N-(2-cyclopentyl)-4-phenoxy-6-isopropyl)phenyl-N'-isopropylthiourea are charged to 50 ml of ethanol, 2.7 g of methyl iodide are added at room temperature, and the reaction mixture is stirred for 6 hours at 40° C. The reaction solution is then cooled, poured into 400 ml of water and the resultant yellow precipitate is isolated by filtration. The residue is dried and recrystallised from a 1:2 mixture of ethanol/water. The product melts at 175.5°–177° C.

The following compounds are prepared in analogous manner:

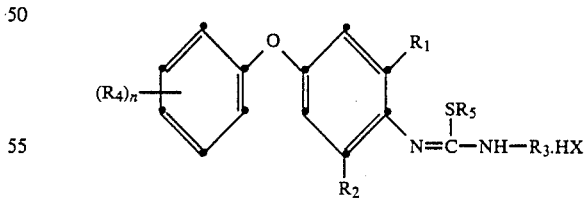

| Compound | n | R₁ | R₂ | R₃ | R₄ | R₅ | HX | Physical data |
|---|---|---|---|---|---|---|---|---|
| 1.2.2.2. | 1 | cyclohexyl | $C_2H_5$ | $C(CH_3)_3$ | H | $CH_3$ | — | resin |
| 1.2.2.3. | 1 | cyclopentyl | $CH(CH_3)_2$ | $CH(CH_3)_2$ | H | $CH_3$ | HJ | m.p. 175.5–177° C. |
| 1.2.2.4. | 1 | cyclopentyl | $CH(CH_3)_2$ | $CH(CH_3)_2$ | H | $CH_3$ | — | m.p. 83.5–84.5° C. |
| 1.2.2.5. | 1 | cyclopentyl | $CH(CH_3)_2$ | $C(CH_3)_3$ | H | $CH_3$ | — | m.p. 101.5–102° C. |
| 1.2.2.6. | 1 | cyclopentyl | $C_2H_5$ | $CH(CH_3)_2$ | H | $CH_3$ | — | $n_D^{22.5}$: 1.5822 |
| 1.2.2.7. | 1 | cyclopentyl | $C_2H_5$ | $C(CH_3)_3$ | H | $CH_3$ | — | m.p. 99.5–101° C. |

-continued

| Compound | n | R₁ | R₂ | R₃ | R₄ | R₅ | HX | Physical data |
|---|---|---|---|---|---|---|---|---|
| 1.2.2.8. | 1 | cyclopentyl | CH(CH₃)₂ | C(CH₃)₃ | 4-F | CH₃ | — | m.p. 109–110° C. |
| 1.2.2.9. | 1 | cyclopentyl | CH(CH₃)₂ | CH(CH₃)₂ | 4-F | CH₃ | — | $n_D^{26}$: 1.5675 |
| 1.2.2.10. | 1 | cyclopentyl | C₂H₅ | C(CH₃)₃ | 4-F | CH₃ | — | m.p. 86–87.5° C. |
| 1.2.2.11. | 1 | cyclopentyl | CH(CH₃)₂ | C(CH₃)₃ | 3-F | CH₃ | — | m.p. 111–112.5° C. |
| 1.2.2.12. | 1 | cyclopentyl | CH(CH₃)₂ | CH(CH₃)₂ | 3-F | CH₃ | — | $n_D^{24}$: 1.5670 |
| 1.2.2.13. | 1 | cyclopentyl | C₂H₅ | C(CH₃)₃ | 3-F | CH₃ | — | $n_D^{24}$: 1.5705 |
| 1.2.2.14. | 1 | cyclopentyl | C₂H₅ | CH(CH₃)₂ | 3-F | CH₃ | — | $n_D^{24}$: 1.5720 |
| 1.2.2.15. | 1 | cyclopentyl | CH(CH₃)₂ | C(CH₃)₃ | 2-F | CH₃ | — | amorphous |
| 1.2.2.16. | 1 | cyclopentyl | CH(CH₃)₂ | CH(CH₃)₂ | 2-F | CH₃ | — | amorphous |
| 1.2.2.17. | 1 | cyclopentyl | CH(CH₃)₂ | CH(CH₃)₂ | 2-F | CH₃ | HJ | m.p. 181–182.5° C. |
| 1.2.2.18. | 1 | cyclopentyl | C₂H₅ | C(CH₃)₃ | 2-F | CH₃ | — | $n_D^{24}$: 1.5701 |
| 1.2.2.19. | 1 | cyclopentyl | cyclopentyl | C(CH₃)₃ | H | CH₃ | — | m.p. 75–80° C. |
| 1.2.2.20. | 1 | cyclopentyl | cyclopentyl | CH(CH₃)₂ | H | CH₃ | — | m.p. 60–63.5° C. |
| 1.2.2.21. | 2 | cyclopentyl | CH(CH₃)₂ | CH(CH₃)₂ | 3-F, 5-F | CH₃ | — | $n_D^{21}$: 1.5580 |
| 1.2.2.22. | 1 | cyclopentyl | CH(CH₃)₂ | cyclopentyl | H | CH₃ | — | $n_D^{25}$: 1.5821 |
| 1.2.2.23. | 2 | cyclopentyl | CH(CH₃)₂ | CH(CH₃)₂ | 2-F, 4-F | CH₃ | — | m.p. 67.5–69° C. |
| 1.2.2.24. | 2 | cyclopentyl | CH(CH₃)₂ | C(CH₃)₃ | 2-F, 4-F | CH₃ | — | m.p. 88.5–90° C. |
| 1.2.2.25. | 1 | cyclopentyl | CH(CH₃)₂ | CH(CH₃)C₂H₅ | H | CH₃ | — | $n_D^{25}$: 1.5722 |
| 1.2.2.26. | 1 | cyclopentyl | CH(CH₃)₂ | CH(CH₃)CH(CH₃)₂ | H | CH₃ | — | $n_D^{24}$: 1.5620 |
| 1.2.2.27. | 1 | cyclopentyl | CH(CH₃)₂ | C(CH₃)₂C₂H₅ | H | CH₃ | — | m.p. 101–102° C. |
| 1.2.2.28. | 1 | cyclopentyl | CH(CH₃)₂ | CH(CH₃)cyclopropyl | H | CH₃ | — | $n_D^{24}$: 1.5719 |
| 1.2.2.29. | 1 | cyclopentyl | CH(CH₃)₂ | C(CH₃)₃ | H | C₂H₅ | — | $n_D^{25}$: 1.5620 |
| 1.2.2.30. | 1 | cyclopentyl | CH(CH₃)₂ | CH(CH₃)₂ | H | C₂H₅ | — | $n_D^{24}$: 1.5700 |
| 1.2.2.31. | 1 | cyclopentyl | CH(CH₃)₂ | CH(CH₃)₂ | H | C₂H₅ | HI | m.p. 156–159° C. |
| 1.2.2.32. | 1 | cyclopentyl | CH(CH₃)₂ | CH(CH₃)₂ | H | C₃H₇ | — | $n_D^{25}$: 1.5634 |
| 1.2.2.33. | 1 | cyclopentyl | CH(CH₃)₂ | CH(CH₃)₂ | H | C₄H₉ | — | $n_D^{23}$: 1.5618 |
| 1.2.2.34. | 1 | cyclopentyl | CH(CH₃)₂ | C(CH₃)₃ | H | C₃H₇ | — | m.p. 63.5–64° C. |
| 1.2.2.35. | 1 | cyclopentyl | CH(CH₃)₂ | C(CH₃)₃ | H | C₄H₉ | — | m.p. 35–37° C. |
| 1.2.2.36. | 1 | cyclopentyl | CH₃ | C(CH₃)₃ | H | CH₃ | — | $n_D^{21}$: 1.5762 |
| 1.2.2.37. | 1 | cyclopentyl | CH₃ | CH(CH₃)₂ | H | CH₃ | — | $n_D^{21}$: 1.5850 |
| 1.2.2.38. | 1 | cyclopentyl | CH(CH₃)₂ | Cyclopentyl | H | CH₃ | HI | m.p. 179.5–182° C. |
| 1.2.2.39. | 2 | cyclopentyl | CH(CH₃)₂ | CH(CH₃)₂ | 2-F, 4-F | CH₃ | HI | m.p. 182–183.5° C. |
| 1.2.2.40. | 2 | cyclopentyl | CH(CH₃)₂ | CH(CH₃)₂ | 3-F, 5-F | CH₃ | HI | m.p. 161.5–164° C. |
| 1.2.2.41. | 1 | cyclopentyl | CH(CH₃)₂ | CH(CH₃)C₂H₅ | H | CH₃ | HI | m.p. 162–164° C. |
|  | 1 | cyclopentyl | C₂H₅ | CH(CH₃)₂ | 4-F | CH₃ | — |  |
|  | 1 | cyclopentyl | C₂H₅ | CH(CH₃)₂ | 2-F | CH₃ | — |  |
|  | 1 | cyclopentyl | CH(CH₃)₂ | C(CH₃)₃ | 4-C(CH₃)₃ | CH₃ | — |  |
|  | 1 | cyclopentyl | CH(CH₃)₂ | CH(CH₃)₂ | 4-C(CH₃)₃ | CH₃ | — |  |
|  | 1 | cyclopentyl | CH(CH₃)₂ | C(CH₃)₃ | 4-Cl | CH₃ | — |  |
|  | 1 | cyclopentyl | CH(CH₃)₂ | CH(CH₃)₂ | 4-Cl | CH₃ | — |  |
|  | 1 | cyclopentyl | CH(CH₃)₂ | C(CH₃)₃ | 3-CF₃ | CH₃ | — |  |
|  | 1 | cyclopentyl | CH(CH₃)₂ | CH(CH₃)₂ | 3-CF₃ | CH₃ | — |  |
|  | 2 | cyclopentyl | CH(CH₃)₂ | C(CH₃)₃ | 3-F,5-F | CH₃ | — |  |

1.2.3 Phenoxyphenylcarbodiimides 1.2.3.1 N-(2-Cyclohexyl-4-phenoxy-6-isopropyl)phenyl-N'-tert-butylcarbodiimide 2.6 g of N-(2-cyclohexyl-4-phenoxy-6-isopropyl)phenyl-N'-tert-butylthiourea and 1.9 g of 2-chloro-1-methylpyridinium iodide are charged to 20 ml of dry acetonitrile, then 1.5 g of triethylamine in 20 ml of acetonitrile are added dropwise, with stirring, at room temperature and the reaction mixture is heated for 2½ hours under reflux. The reaction mixture is then concentrated by evaporation and the residue is extracted repeatedly with hexane. The hexane phases are washed thoroughly with water, dried over sodium sulfate and then concentrated by evaporation. The residue is dissolved in hexane and decolourised with silica gel. The title compound of formula

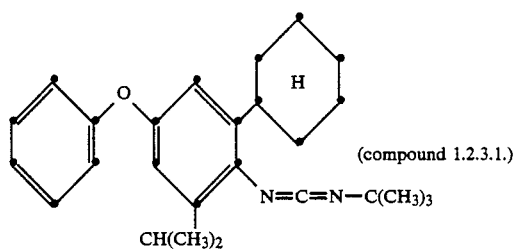

(compound 1.2.3.1.)

is obtained in the form of a yellow oil with a refractive index of $n_D^{24} = 1.5640$.

The following compounds are prepared in analogous manner:

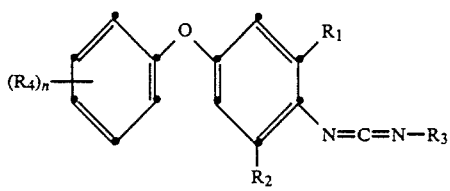

| 2.2. Solutions | (a) | (b) |
|---|---|---|
| a compound according to Preparatory Examples 1.2. | 10% | 5% |
| polyethylene glycol 400 | 70% | — |
| N-methyl-2-pyrrolidone | 20% | 20% |
| epoxidised coconut oil | — | 1% |
| petroleum distillate (boiling range 160–190° C.) | — | 74% |

| Compound | n | R₁ | R₂ | R₃ | R₄ | Phys. data |
|---|---|---|---|---|---|---|
| 1.2.3.2. | 1 | cyclohexyl | $C_2H_5$ | $C(CH_3)_3$ | H | $n_D^{25}$ : 1.5695 |
| 1.2.3.3. | 1 | cyclopentyl | $CH(CH_3)_2$ | $CH(CH_3)_2$ | H | $n_D^{23}$ : 1.5728 |
| 1.2.3.4. | 1 | cyclopentyl | $CH(CH_3)_2$ | $C(CH_3)_3$ | H | $n_D^{24}$ : 1.5670 |
| 1.2.3.5. | 1 | cyclopentyl | $C_2H_5$ | $CH(CH_3)_2$ | H | $n_D^{22}$ : 1.5790 |
| 1.2.3.6. | 1 | cyclopentyl | $C_2H_5$ | $C(CH_3)_3$ | H | $n_D^{24}$ : 1.5715 |
| 1.2.3.7. | 1 | cyclopentyl | $CH(CH_3)_2$ | $C(CH_3)_3$ | 4-F | $n_D^{26}$ : 1.5570 |
| 1.2.3.8. | 1 | cyclopentyl | $CH(CH_3)_2$ | $CH(CH_3)_2$ | 4-F | $n_D^{24}$ : 1.5630 |
| 1.2.3.9. | 1 | cyclopentyl | $C_2H_5$ | $C(CH_3)_3$ | 4-F | $n_D^{23}$ : 1.5630 |
| 1.2.3.10. | 1 | cyclopentyl | $CH(CH_3)_2$ | $C(CH_3)_3$ | 3-F | $n_D^{23}$ : 1.5585 |
| 1.2.3.11. | 1 | cyclopentyl | $CH(CH_3)_2$ | $CH(CH_3)_2$ | 3-F | $n_D^{23}$ : 1.5640 |
| 1.2.3.12. | 1 | cyclopentyl | $C_2H_5$ | $C(CH_3)_3$ | 3-F | $n_D^{27}$ : 1.5604 |
| 1.2.3.13. | 1 | cyclopentyl | $C_2H_5$ | $CH(CH_3)_2$ | 3-F | $n_D^{26}$ : 1.5660 |
| 1.2.3.14. | 1 | cyclopentyl | $CH(CH_3)_2$ | $C(CH_3)_3$ | 2-F | $n_D^{21}$ : 1.5578 |
| 1.2.3.15. | 1 | cyclopentyl | $CH(CH_3)_2$ | $CH(CH_3)_2$ | 2-F | $n_D^{21}$ : 1.5642 |
| 1.2.3.16. | 1 | cyclopentyl | $C_2H_5$ | $C(CH_3)_3$ | 2-F | $n_D^{24}$ : 1.5632 |
| 1.2.3.17. | 1 | cyclopentyl | cyclopentyl | $C(CH_3)_3$ | H | $n_D^{23}$ : 1.5741 |
| 1.2.3.18. | 1 | cyclopentyl | cyclopentyl | $CH(CH_3)_2$ | H | $n_D^{21}$ : 1.5831 |
| 1.2.3.19. | 1 | cyclopentyl | $CH(CH_3)_2$ | cyclopentyl | H | $n_D^{24}$ : 1.5810 |
| 1.2.3.20. | 2 | cyclopentyl | $CH(CH_3)_2$ | $CH(CH_3)_2$ | 2-F, 4-F | $n_D^{26}$ : 1.5513 |
| 1.2.3.21. | 2 | cyclopentyl | $CH(CH_3)_2$ | $C(CH_3)_3$ | 2-F, 4-F | $n_D^{26}$ : 1.5471 |
| 1.2.3.22. | 1 | cyclopentyl | $CH(CH_3)_2$ | $CH(CH_3)C_2H_5$ | H | $n_D^{24}$ : 1.5690 |
| 1.2.3.23. | 1 | cyclopentyl | $CH(CH_3)_2$ | $CH(CH_3)CH(CH_3)_2$ | H | $n_D^{25}$ : 1.5650 |
| 1.2.3.24. | 1 | cyclopentyl | $CH(CH_3)_2$ | $CH(CH_3)$cyclopropyl | H | $n_D^{25}$ : 1.5717 |
| 1.2.3.25. | 1 | cyclopentyl | $CH(CH_3)_2$ | $C(CH_3)_2C_2H_5$ | H | $n_D^{24}$ : 1.5642 |
|  | 1 | cyclopentyl | $C_2H_5$ | $CH(CH_3)_2$ | 4-F |  |
|  | 1 | cyclopentyl | $C_2H_5$ | $CH(CH_3)_2$ | 2-F |  |
|  | 2 | cyclopentyl | $CH(CH_3)_2$ | $C(CH_3)_3$ | 3-F, 5-F |  |
|  | 1 | cyclopentyl | $CH_3$ | $C(CH_3)_3$ | H |  |
|  | 1 | cyclopentyl | $CH_3$ | $CH(CH_3)_2$ | H |  |
|  | 1 | cyclopentyl | $CH(CH_3)_2$ | $C(CH_3)_3$ | 4-$C(CH_3)_3$ |  |
|  | 1 | cyclopentyl | $CH(CH_3)_2$ | $CH(CH_3)_2$ | 4-$C(CH_3)_3$ |  |
|  | 1 | cyclopentyl | $CH(CH_3)_2$ | $C(CH_3)_3$ | 4-Cl |  |
|  | 1 | cyclopentyl | $CH(CH_3)_2$ | $CH(CH_3)_2$ | 4-Cl |  |
|  | 1 | cyclopentyl | $CH(CH_3)_2$ | $C(CH_3)_3$ | 3-$CF_3$ |  |
|  | 1 | cyclopentyl | $CH(CH_3)_2$ | $CH(CH_3)_2$ | 3-$CF_3$ |  |

EXAMPLE 2

Formulations of Compounds of Formula I According to Preparatory Examples 1.2. (throughout, percentages are by weight)

| 2.1. Emulsifiable concentrates | (a) | (b) |
|---|---|---|
| a compound according to Preparatory Examples 1.2. | 10% | 25% |
| calcium dodecylbenzenesulfonate | — | 5% |
| castor oil polyethylene glycol ether (36 mol of ethylene oxide) | 25% | 5% |
| tributylphenol polyethylene glycol ether (30 mol of ethylene oxide) | — | — |
| cyclohexanone | — | 40% |
| butanol | 15% | — |
| xylene mixture | — | 25% |
| ethyl acetate | 50% | — |

Emulsions of any required concentration can be produced from such concentrates by dilution with water.

These solutions are suitable for application in the form of microdrops.

| 2.3. Granulates | (a) | (b) |
|---|---|---|
| a compound according to Preparatory Examples 1.2. | 5% | 10% |
| kaolin | 94% | — |
| highly dispersed silicic acid | 1% | — |
| attapulgite | — | 90% |

The active ingredient or ingredients is or are dissolved in methylene chloride, the solution is sprayed onto the carrier, and the solvent is subsequently evaporated off in vacuo.

| 2.4. Extruder granulate |  |
|---|---|
| a compound according to Preparatory Examples 1.2. | 10% |
| sodium lignosulfonate | 2% |
| carboxymethylcellulose | 1% |

-continued

| 2.4. Extruder granulate | |
|---|---|
| kaolin | 87% |

The active ingredient or ingredients is or are mixed and ground with the adjuvants, and the mixture is subsequently moistened with water. The mixture is extruded and then dried in a stream of air.

| 2.5. Coated granulate | |
|---|---|
| a compound according to Preparatory Examples 1.2. | 3% |
| polyethylene glycol 200 | 3% |
| kaolin | 94% |

The finely ground active ingredient is uniformly applied, in a mixer, to the kaolin moistened with polyethylene glycol. Non-dusty coated granulates are obtained in this manner.

| 2.6 Dusts | (a) | (b) | (c) | (d) |
|---|---|---|---|---|
| a compound according to Preparatory Examples 1.2. | 2% | 5% | 5% | 8% |
| highly dispersed silicic acid | 1% | 5% | — | — |
| talcum | 97% | — | 95% | — |
| kaolin | — | 90% | — | 92% |

Ready-for-use dusts are obtained by intimately mixing the carriers with the active ingredient and, optionally, grinding the mixture in a suitable mill.

| 2.7. Wettable powders | (a) | (b) | (c) |
|---|---|---|---|
| a compound according to Preparatory Examples 1.2. | 20% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7-8 mol of ethylene oxide) | — | 2% | — |
| highly dispersed silicic acid | 5% | 10% | 10% |
| kaolin | 67% | 27% | — |

The active ingredient is thoroughly mixed with the adjuvants and the mixture is thoroughly ground in a suitable mill, affording wettable powders which can be diluted with water to give suspensions of the desired concentration.

| 2.8. Suspension concentrate | |
|---|---|
| a compound according to Preparatory Examples 1.2. | 40% |
| ethylene glycol | 10% |
| nonylphenol polyethylene glycol (15 mol of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

EXAMPLE 3 Biological Tests 3.1. Action against Musca domestica

A sugar lump is moistened with a solution of the test compound in an amount sufficient to give a concentration of 500 ppm of active ingredient in the dried lump. The treated sugar lump is placed in a dish together with a wet cotton wool swab and covered with a glass beaker. Ten adult one-week-old and OP-resistant flies are then placed beneath the beaker and kept at 25° C. and 50% humidity. The insecticidal activity is evaluated by determining mortality after 24 hours.

Compounds of Examples 1.2.1., 1.2.2. and 1.2.3 exhibit good activity in this test.

3.2 Action against Lucilia sericata 1 ml of an aqueous formulation containing 0.5% of test compound is added at 50° C. to 9 ml of a culture medium. Then about 30 freshly hatched Lucilia sericata larvae are added to the culture medium, and the insecticidal action is determined after 48 and 96 hours by evaluating the mortality rate.

In this test, compounds of Examples 1.2.1., 1.2.2. and 1.2.3. exhibit good activity against Lucilia sericata.

3.3. Action against ectoparasiticidal ticks

Ten Boophilus microplus females which are freshly replete with blood are affixed in a row in the dorsal position to a PVC plate and covered with a cottonwool swab. The swab is then impregnated with 10 ml of an aqueous solution of the test compound. One hour later the cottonwool swab is removed and the ticks are dried overnight at 24° C. After drying, the ticks are kept for 4 weeks at 28° C. and 80% relative humidity until oviposition is complete and the larvae have started to hatch.

Each test compound is applied in a concentration of 500 ppm. Acaricidal activity takes the form of either mortality or sterility of the female or of blockage of embryogenesis in the egg deposit or inhibition of hatching. All compounds are tested against two strains of tick, viz. the OP-resistant BIARRA strain and the amidine-resistant ULAM strain.

Compounds of Examples 1.2.1, 1.2.2. and 1.2.3. exhibit good activity in this test.

3.4. Stomach toxicant action against Spodoptera littoralis larvae $L_1$

Cotton plants in the cotyledon stage are sprayed with an aqueous emulsion (obtained from a 10% emulsifiable concentrate) containing 400 ppm of the test compound. After the spray coating has dried, each cotton plant is populated with Spodoptera littoralis larvae in the $L_1$-stage. The test is carried out at 26° C. and ca. 50% relative humidity. After 2 and 3 days a mortality count is made and, after 5 days, the larvae are also examined for inhibition of development and moulting.

Compounds of Examples 1.2.1, 1.2.2 and 1.2.3. exhibit good activity in this test.

3.5. Stomach poison action against Spodoptera littoralis and Heliothis vireschens larvae ($L_3$)

Potted soybean plants (pot size: 10 cm diameter) in the 4-leaf stage are sprayed with aqueous emulsions which contain the test compound in concentrations of 50 to 400 ppm.

After 2 days, each treated soybean plant is populated with 10 larvae of Spodoptera littoralis and Heliothis virescens in the $L_3$-stage. The test is carried out at 26° C. and ca. 60% relative humidity in dim light. After 2 and 5 days evaluation is made to determine the percentage mortality of the larvae.

Compounds of Examples 1.2.1., 1.2.2. and 1.2.3. exhibit good activity in this test.

3.6. Insecticidal stomach poison action against Plutella xylostella larvae ($L_2$)

Potted Chinese cabbage plants (pot size: 10 cm diameter) in the 4-leaf stage are sprayed with aqueous emulsions which contain the test compound in concentrations of 50 to 400 ppm.

After 2 days, each treated Chinese cabbage plant is populated with 10 Plutella xylostella larvae in the $L_2$-stage. The test is carried out at 26° C. and ca. 60% relative humidity in dim light. After 2 and 5 days evaluation is made to determine the percentage mortality of the larvae.

Compounds of Examples 1.2.1, 1.2.2. and 1.2.3. exhibit good activity in this test.

3.7. Contact action against Nilaparvata lugens (nymphs)

The test is carried out with growing plants. For this purpose 4 rice plants (ca. 20 days old), about 15 cm in height, are planted into each of a number of pots (diameter 5.5 cm). The plants in each pot are sprayed on a rotary table with 40 ml of an acetonic solution containing 400 ppm of the respective test compound. After the spray coating has dried, each plant is populated with 20 nymphs of the test organisms in the second or third stage. To prevent the cicadas from escaping, a glass cylinder is slipped over each of the plants and sealed with a gauze top. The nymphs are kept for 6 days on the treated plant, which has to be watered at least once. The test is carried out at about 23° C. and 55% relative humidity and the plants are exposed to light for 16 hours.

Compounds of Examples 1.2.1., 1.2.2. and 1.2.3. exhibit good activity in this test.

3.8. Systemic action against Nilaparvata lugens

Rice plants which are about 10 days old and about 10 cm high are put into a plastic beaker which contains 20 ml of an aqueous emulsion formulation of the test compound in a concentration of 100 ppm and which is sealed with a perforated plastic lid. The root of each rice plant is pushed through a hole in the plastic lid into the aqueous test formulation. The perforation is sealed with cottonwool in order to fix the plant and to protect the test formulation from contact with the gas phase. The rice plant is then populated with 20 nymphs of Nilaparvata lugens in the $N_2$–$N_3$ stage and covered with a plastic cylinder. The test is carried out at 26° C. and ca. 60% relative humidity and the plant is exposed to light for 16 hours. A mortality count is made 2 and 5 days later, using untreated controls for comparison purposes, thereby establishing whether the test compound absorbed through the root kills the test organisms on the upper parts of the plant.

Compounds of Examples 1.2.1., 1.2.2. and 1.2.3. effect 80–100% kill of Nilaparvata lugens in this test.

3.9. Action against soil insects (Diabrotica balteata)

350 ml of soil (consisting of 95 vol. % of sand and 5 vol. % of peat) are mixed with 150 ml of an aqueous emulsion formulation which contains the test compound in a concentration of 400 ppm. Plastic beakers with a diameter of about 10 cm at the top are then partly filled with the treated soil. Ten $L_3$-larvae of Diabrotica balteata are put into each beaker, then 4 maize seedlings are planted and the beaker is filled up with soil. The beakers are sealed with plastic sheeting and kept at about 24° C. and ca. 50% relative humidity. Six days later the soil in the beakers is sieved and a mortality count of the remaining larvae is made.

Compounds of Examples 1.2.1, 1.2.2. and 1.2.3. exhibit good activity in this test.

3.10. Contact action against Aphis craccivora

Before the start of the test, 4- to 5-day old bean seedlings (Vicia faba) grown in pots are each populated with about 200 insects of the species Aphis craccivora. The treated plants are sprayed direct to drip point 24 hours later with an aqueous formulation containing 400 ppm of the test compound. Two plants are used for each test compound at its given concentration. A mortality count is made after 3 and 5 days respectively. The test is carried out at ca. 21° C. and at a relative humidity of about 55%.

Compounds of Examples 1.2.1., 1.2.2. and 1.2.3. exhibit good activity in this test.

3.11. Contact action against Myzus persicae 4- to 5-day old bean seedlings (Vicia faba) which have been cultivated in water are each populated with about 200 aphids of the species Myzus persicae before the start of the test. The treated plants are sprayed direct to drip point 24 hours later with an aqueous suspension containing the test compound in a concentration of 100 ppm. Two plants are used for each compound at its given concentration. An evaluation of percentage mortality is made 3 and 5 days respectively after application. The test is carried out at ca. 21° C. and ca. 60% relative humidity.

Compounds of Examples 1.2.1., 1.2.2. and 1.2.3. exhibit good activity in this test.

3.12. Action against Tetranychus urticae (OP-sensitive)

24 hours before the test for acaricidal action, the primary leaves of Phaseolus vulgaris plants are infected with an infested piece of leaf from a mass culture of Tetranychus urticae (OP-sensitive) (mixed population). The tolerance refers to the tolerance to diazinone. The treated infested plants are sprayed to drip point with a test solution in emulsion form containing the respective test compound in a concentration of 400 ppm. During the test run the plants are kept in greenhouse compartments at ca. 25° C. and ca. 50% relative humidity. A count of the number of living and dead imagines and larvae (all mobile stages) is made under a stereoscopic microscope after 6 days.

Compounds of Examples 1.2.1., 1.2.2. and 1.2.3. exhibit good activity in this test.

3.13. Action against Panonychus ulmi (OP and carbamate resistant)

Potted apple seedlings with about 20 to 30 leaves are each populated with 60 adult females of Panonychus ulmi. The infested plants are sprayed after 7 days to drip point with an aqueous emulsion containing 100 ppm of the test compound. The treated plants are then stood in a greenhouse for a further 14 days at ca. 25° C. and about 50% relative humidity.

After this time, evaluation is made by taking 20 leaves from each plant, removing the mite population from these leaves by means of a brushing device and counting the number of eggs, postembryonic stages and adults under a stereoscopic microscope. An assessment is made of the percentage reduction of the mite population as compared with untreated controls.

Compounds of Examples 1.2.1., 1.2.2. and 1.2.3. exhibit good activity in this test.

3.14. Action against Anthonomus grandis (adults)

Two cotton plants in the 6-leaf stage, in pots, are each sprayed with a wettable aqueous emulsion formulation containing 100 ppm of the test compound. After the spray coating has dried (about 1½ hours), each plant is populated with 10 adult beetles (Anthonomus grandis). Plastic cylinders, covered at the top with gauze, are then slipped over the treated plants populated with the test insects to prevent the beetles from migrating from the plants. The treated plants are then kept at 25° C. and about 60% relative humidity. Evaluation is made after 2, 3, 4 and 5 days to determine the percentage mortality of the beetles (percentage in dorsal position) as well as the anti-feeding action as compared with untreated controls.

Compounds of Examples 1.2.1., 1.2.2. and 1.2.3. exhibit good activity in this test.

3.15. Action against sensitive and resistant adults of Bemisia tabaci

Cotton leaves are immersed in a test solution containing 400 ppm of the test compound. The treated, dry leaves are placed in covered petri dishes and populated with 20–50 sensitive and resistant adults of Bemisia tabaci. A mortality count is made 20 hours later.

Compounds of Examples 1.2.1., 1.2.2. and 1.2.3. exhibit good activity in this test.

What is claimed is:

1. A compound of formula I

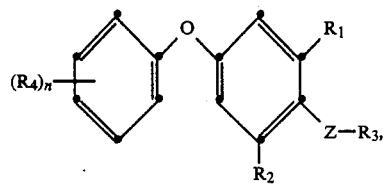

wherein
$R_1$ is $C_3$-$C_7$cycloalkyl or $C_5$-$C_6$cycloalkenyl,
$R_2$ is $C_1$-$C_6$alkyl, $C_5$-$C_6$cycloalkyl or $C_5$-$C_6$cycloalkenyl,
$R_3$ is $C_1$-$C_8$alkyl, $C_3$-$C_6$cycloalkyl, 1-cyclopropylethyl or $C_3$-$C_5$alkenyl,
$R_4$ is hydrogen, halogen, $C_1$-$C_4$alkyl, $C_1$-$C_3$alkoxy or $CF_3$,
n is an integer from 1 to 3,
Z is —NH—CS—NH—, —N=C(SR$_5$)—NH— or —N=C=N—, and
$R_5$ is $C_1$-$C_5$alkyl or allyl
or a salt thereof with an organic or inorganic acid.

2. A compound of formula I according to claim 1, wherein $R_1$ is $C_3$-$C_7$cycloalkyl, $R_2$ is $C_1$-$C_4$alkyl or cyclopentyl, $R_3$ is $C_1$-$C_4$alkyl or $C_3$-$C_5$cycloalkyl, $R_4$ is hydrogen, halogen or $C_1$-$C_3$alkyl, n is 1 or 2, Z is —NH—CS—NH—, —N=C(SR$_5$)—NH— or —N=C=N—, and $R_5$ is $C_1$-$C_3$alkyl.

3. A compound of formula I according to claim 2, wherein $R_1$ is $C_5$-$C_6$cycloalkyl, $R_2$ is ethyl or isopropyl, $R_3$ is isopropyl, tert-butyl or cyclopentyl, $R_4$ is hydrogen or fluorine, n is 1 or 2, and Z is —NH—CS—NH—.

4. A compound of formula I according to claim 2, wherein $R_1$ is $C_5$-$C_6$cycloalkyl, $R_2$ is ethyl or isopropyl, $R_3$ is isopropyl, tert-butyl or cyclopentyl, $R_4$ is hydrogen or fluorine, n is 1 or 2, Z is —N=C(SR$_5$)—NH—, and $R_5$ is methyl or ethyl.

5. A compound of formula I according to claim 2, wherein $R_1$ is $C_5$-$C_6$cycloalkyl, $R_2$ is ethyl or isopropyl, $R_3$ is isopropyl, tert-butyl or cyclopentyl, $R_4$ is hydrogen or fluorine, n is 1 or 2, and Z is —N=C=N—.

6. The compound according to claim 1 of formula

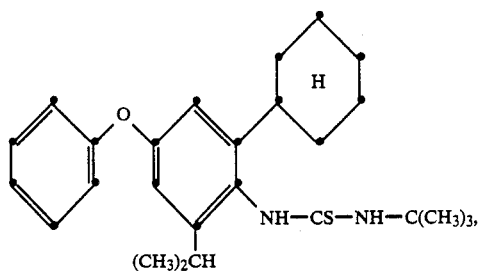

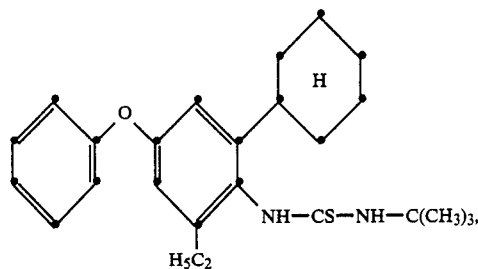

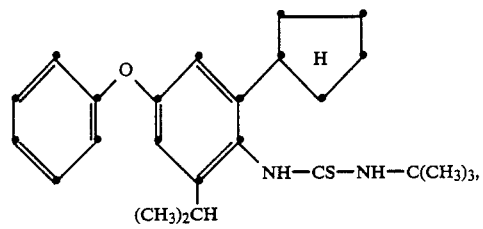

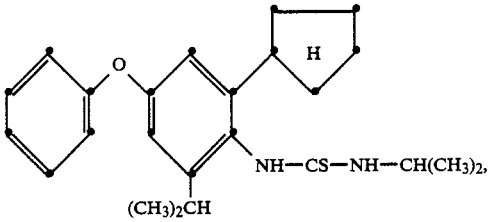

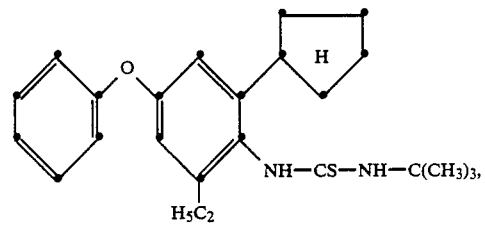

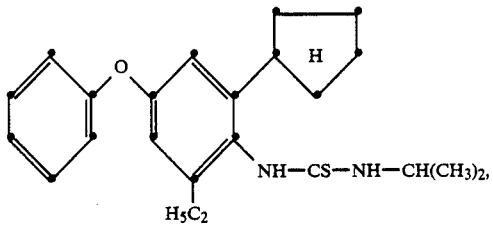

-continued
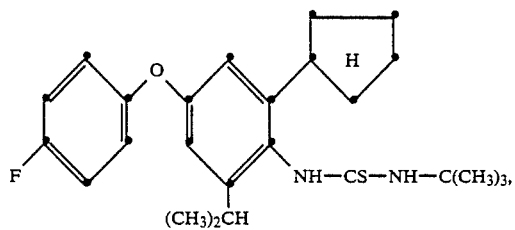
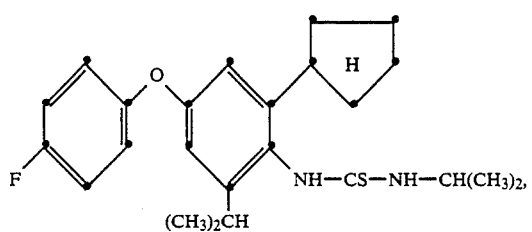
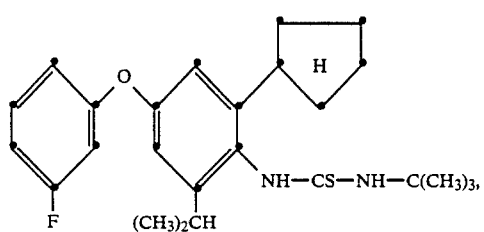
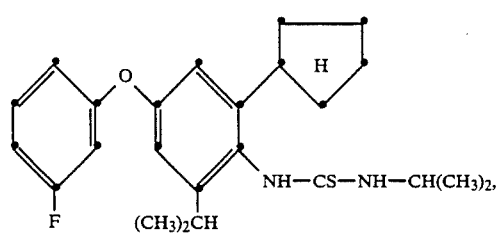
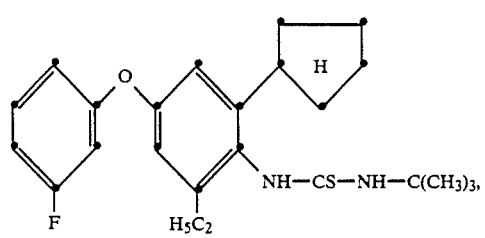
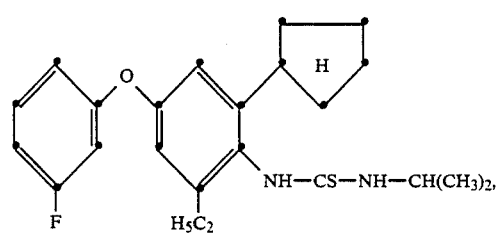
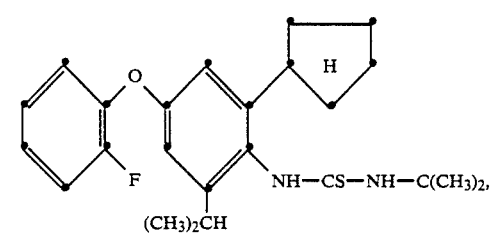
-continued
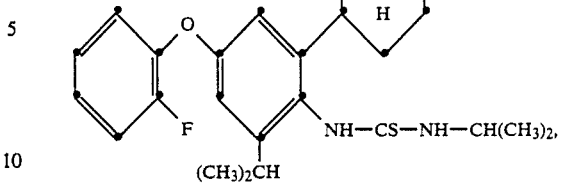
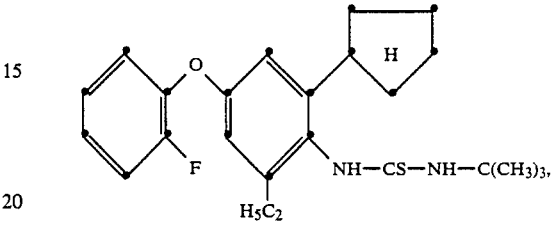
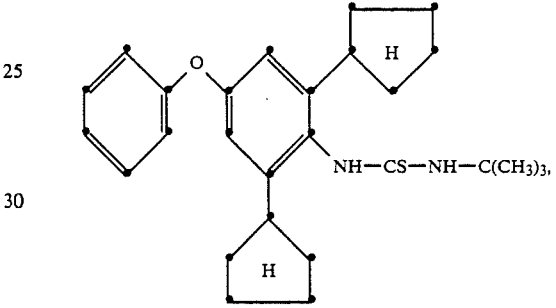
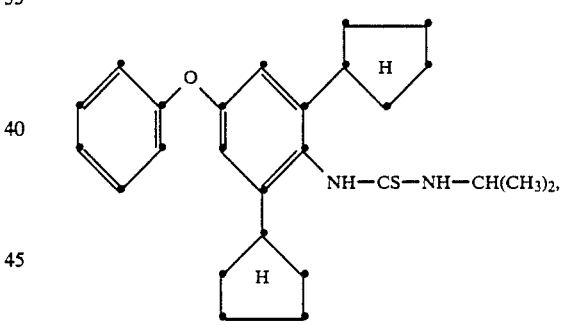
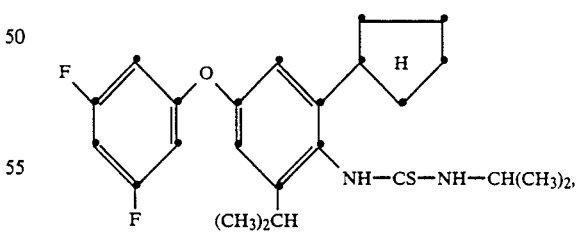
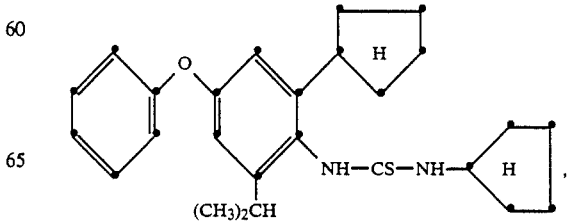

-continued
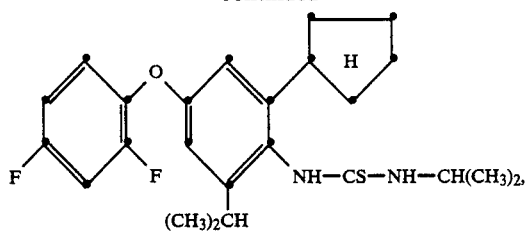
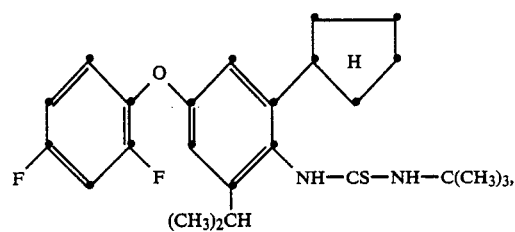
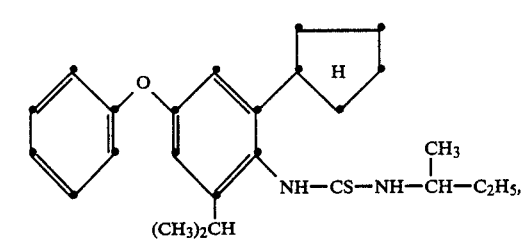
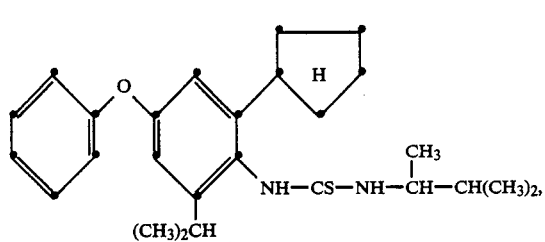
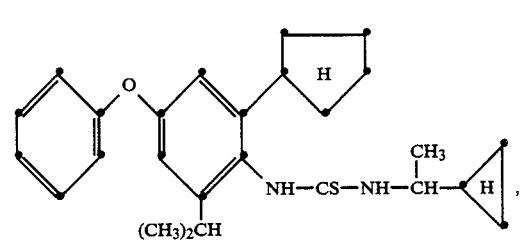
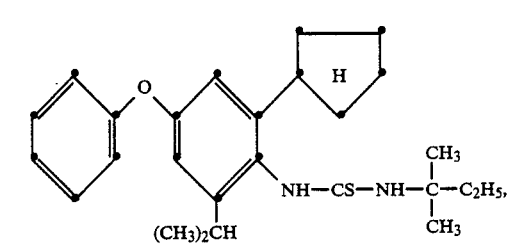
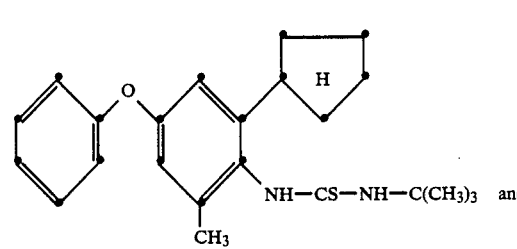
-continued
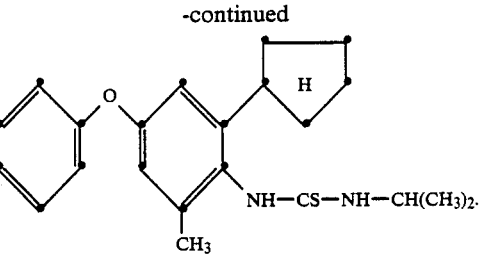
7. The compound according to claim 1 of formula
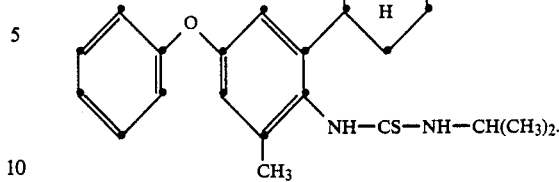
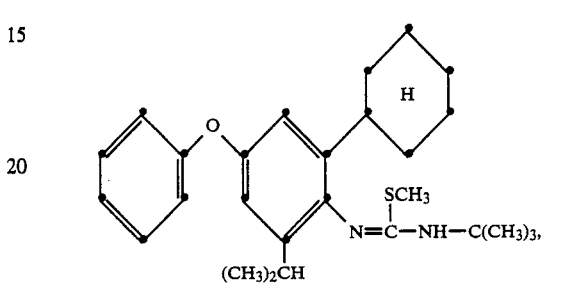
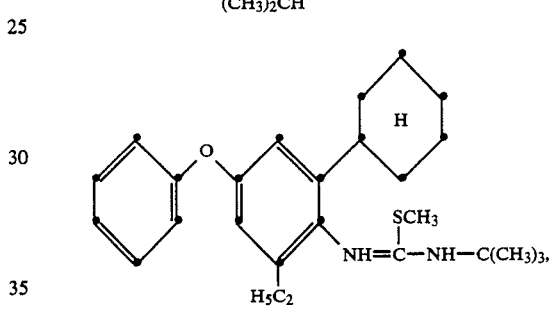
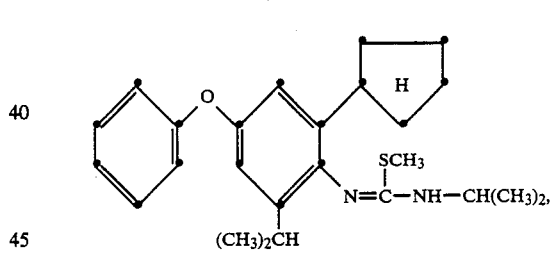
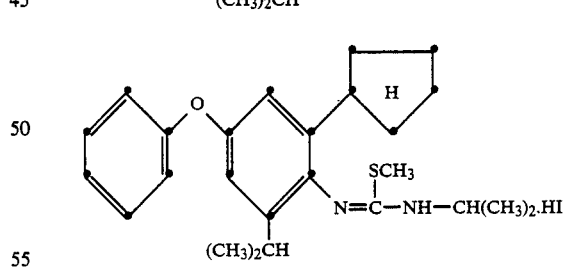
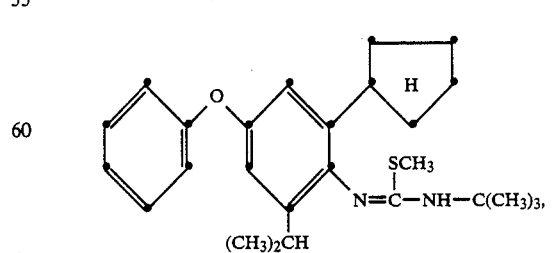

-continued
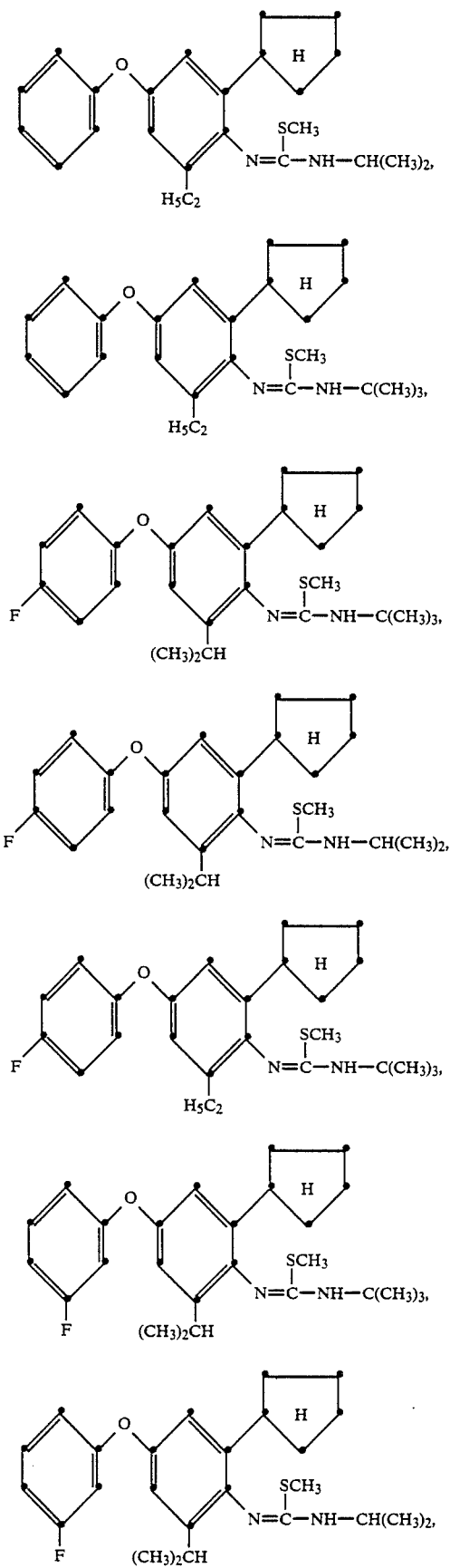
-continued
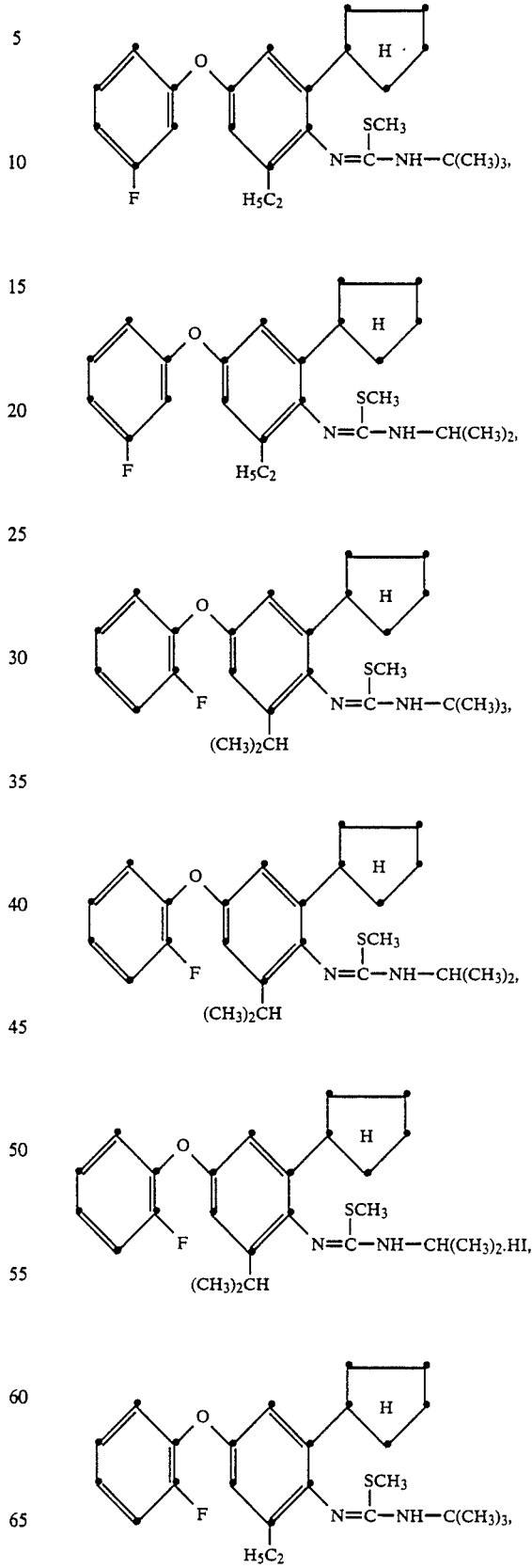

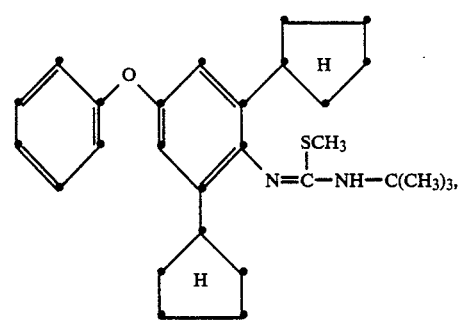
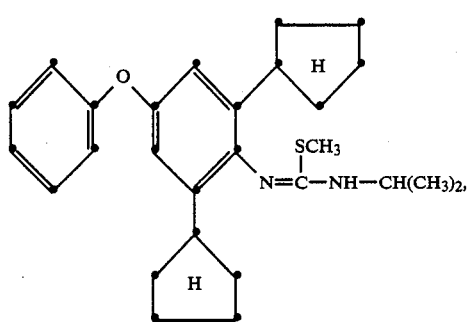
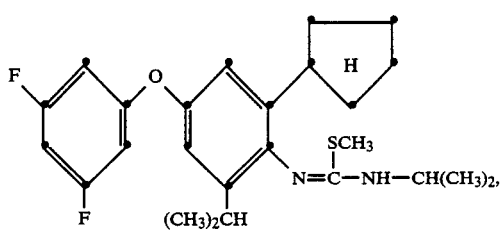
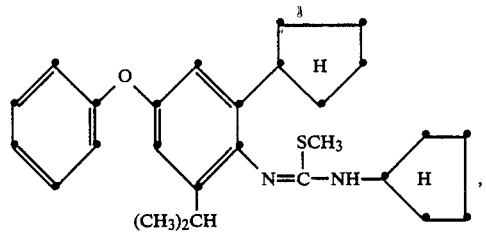
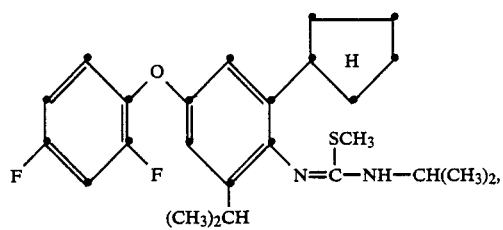
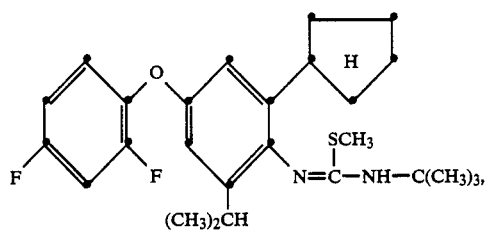
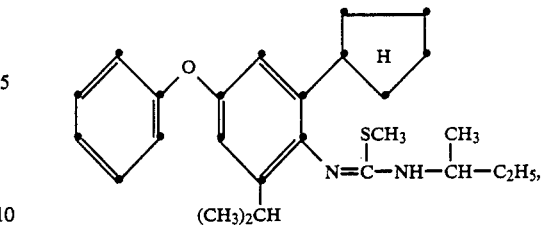
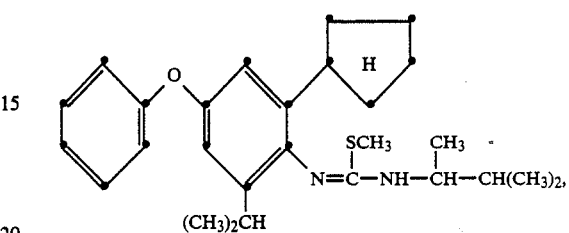
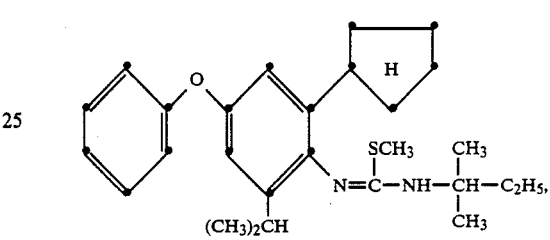
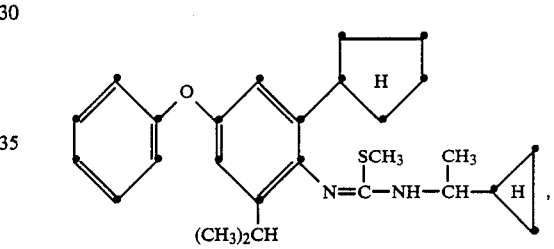
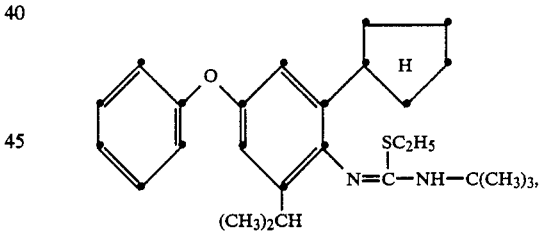
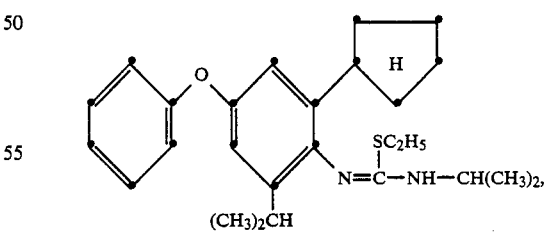
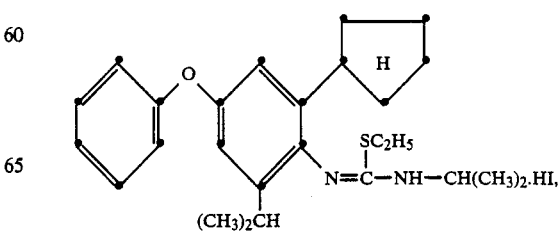

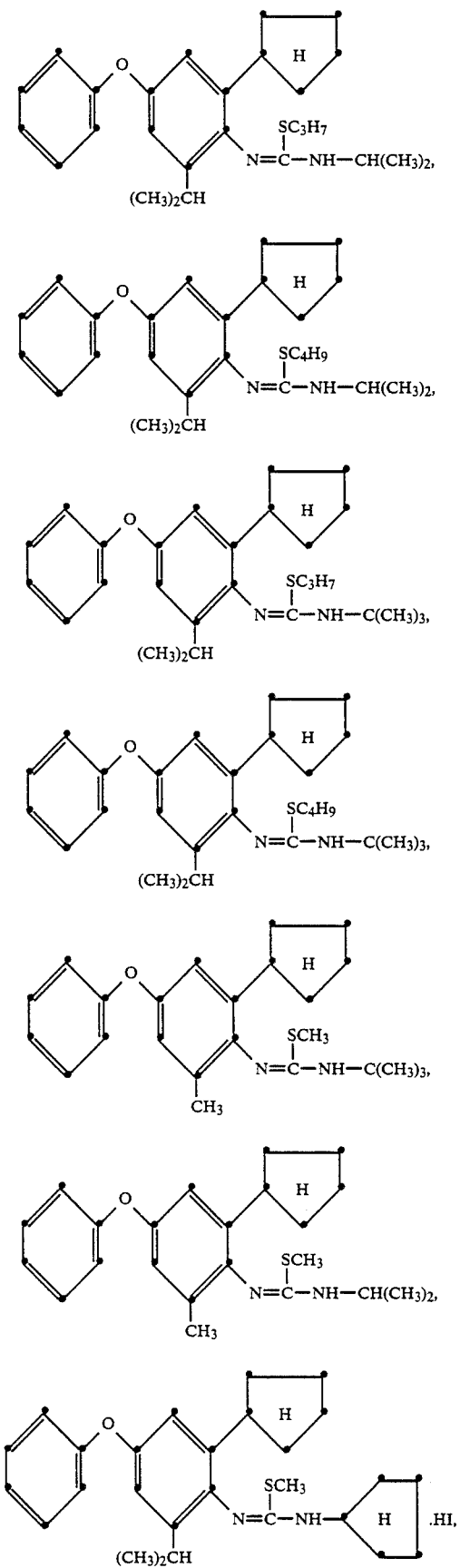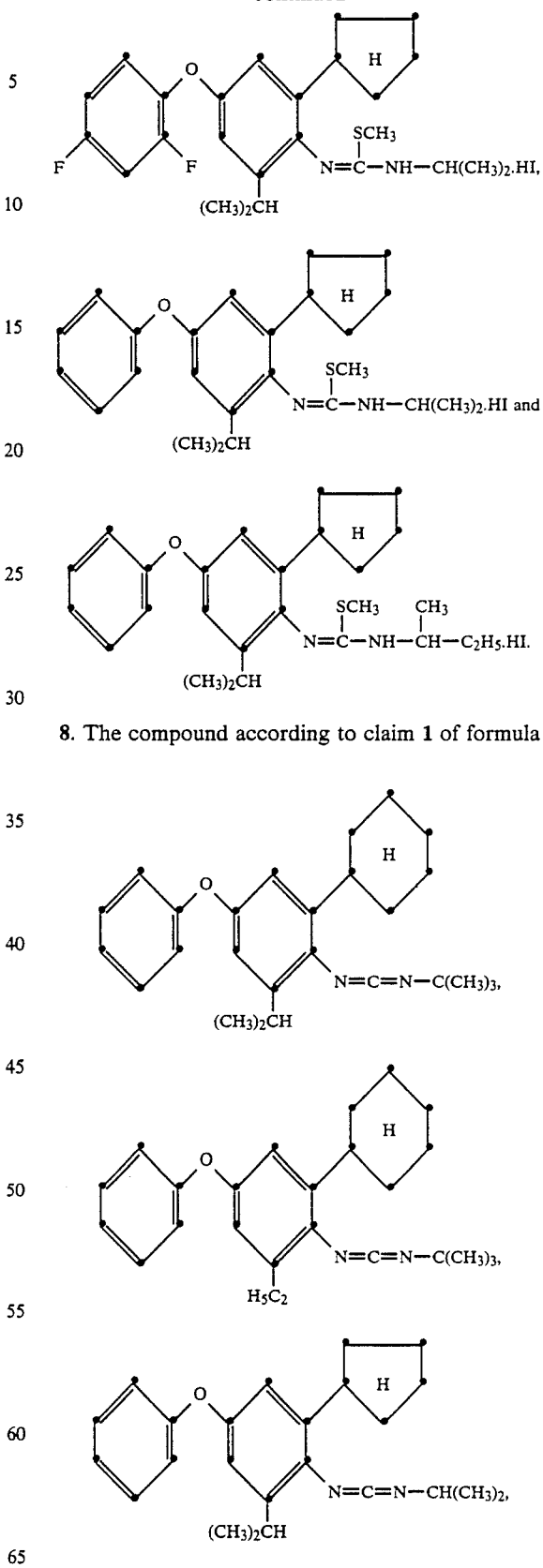
8. The compound according to claim 1 of formula

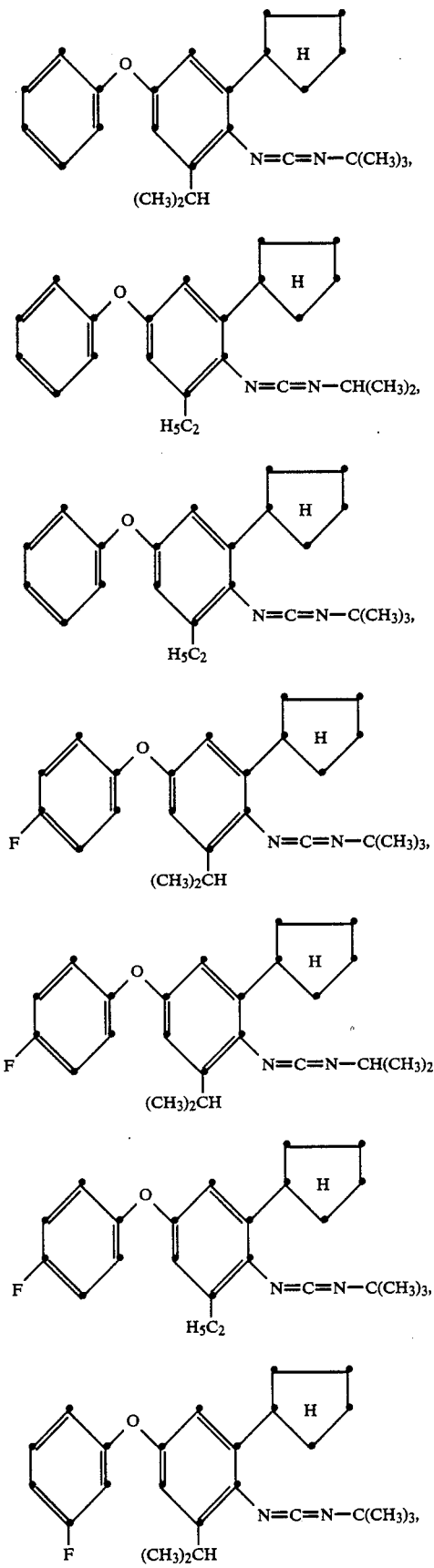
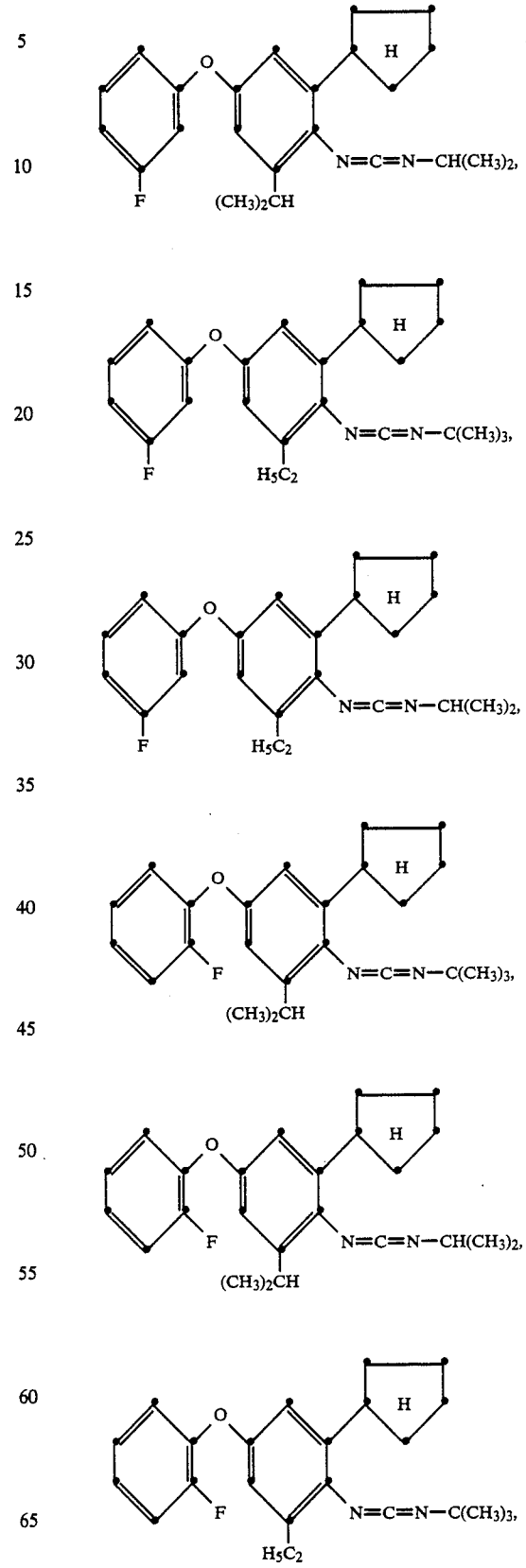

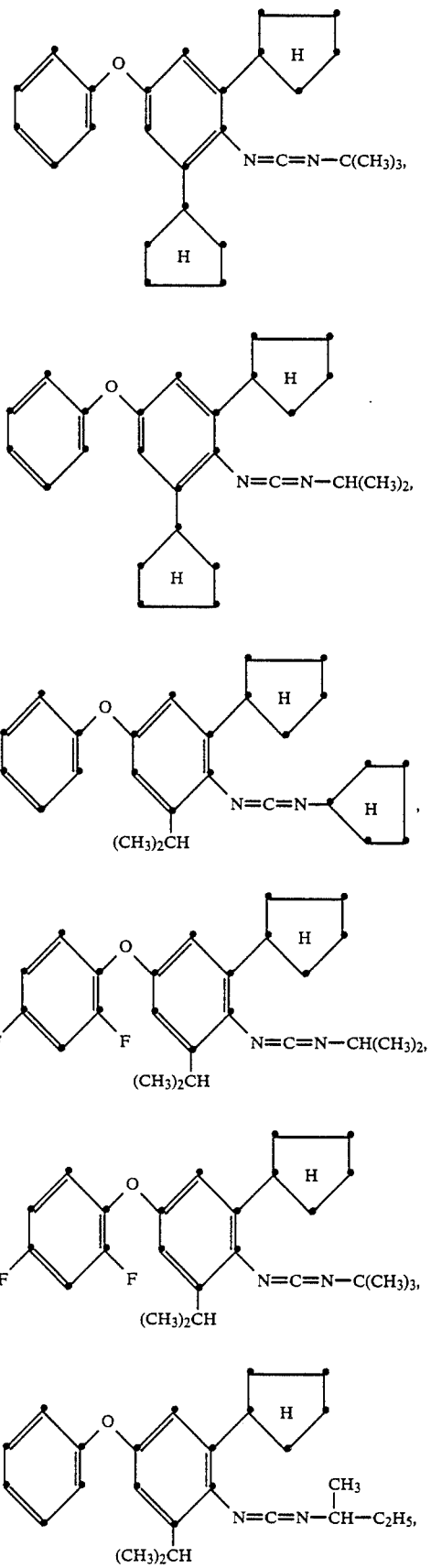

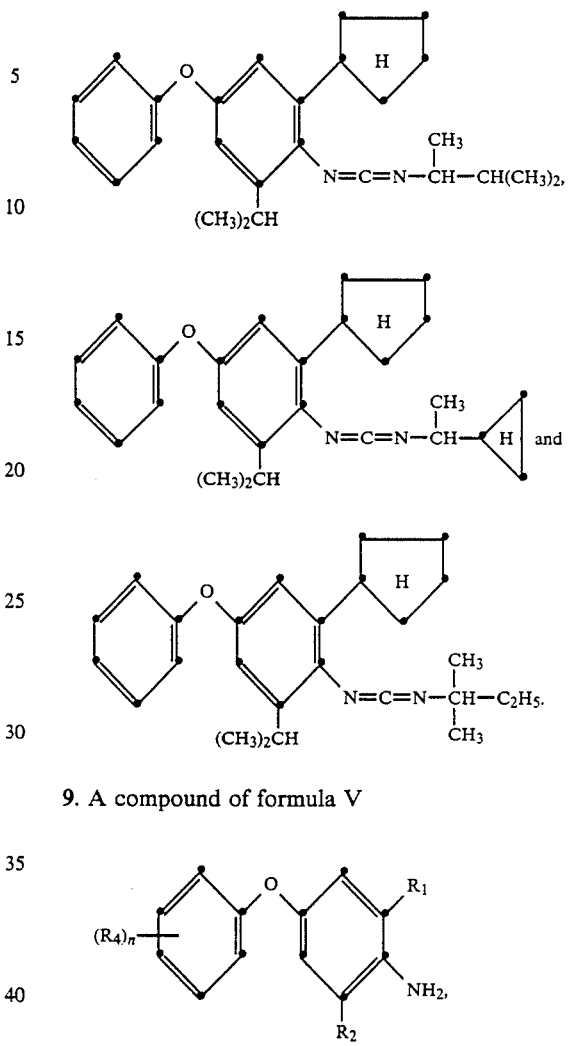

9. A compound of formula V $$\text{(V)}$$

wherein
$R_1$ is $C_3$-$C_7$cycloalkyl or $C_5$-$C_6$cycloalkenyl,
$R_2$ is $C_1$-$C_6$alkyl, $C_5$-$C_6$cycloalkyl or $C_5$-$C_6$cycloalkenyl,
$R_4$ is hydrogen, halogen, $C_1$-$C_4$alkyl, $C_1$-$C_3$alkoxy or $CF_3$,
n is an integer from 1 to 3.

10. A compound of formula V according to claim 9, wherein $R_1$ is $C_3$-$C_7$cycloalkyl, $R_2$ is $C_1$-$C_4$alkyl or cyclopentyl, $R_4$ is hydrogen, halogen or $C_1$-$C_3$alkyl, n is 1 or 2.

11. A compound of formula V according to claim 10, wherein $R_1$ is $C_3$-$C_6$cycloalkyl, $R_2$ is ethyl or isopropyl, $R_4$ is hydrogen or fluorine, n is 1 or 2.

12. The compound according to claim 10 of formula

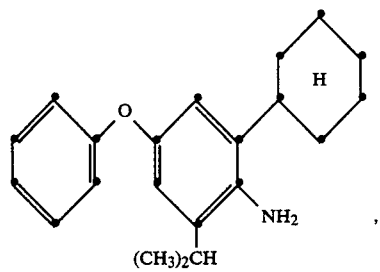,
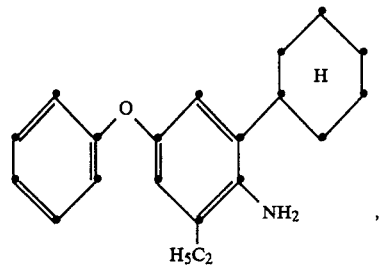,
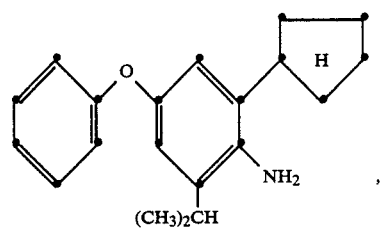,
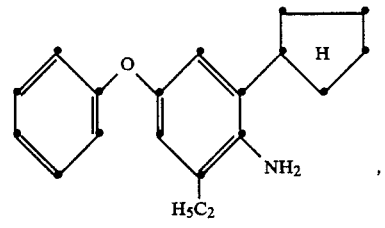,
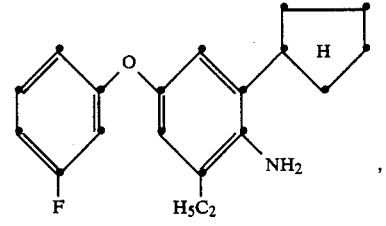,
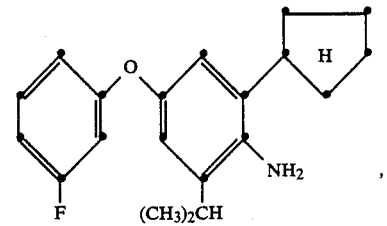,
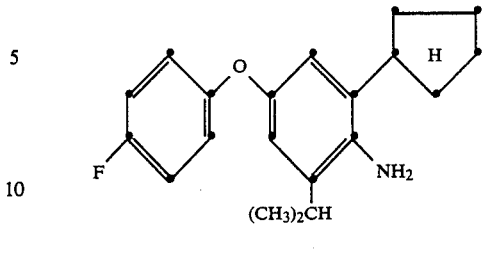,
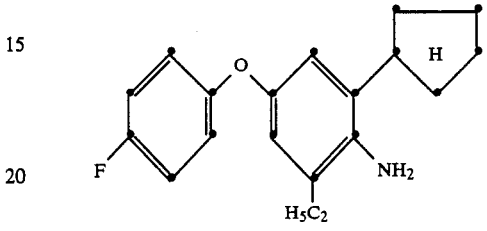,
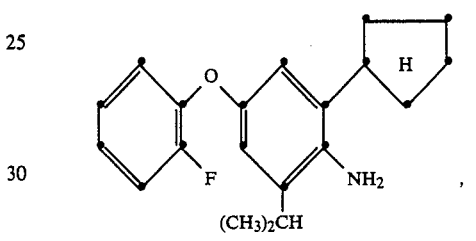,
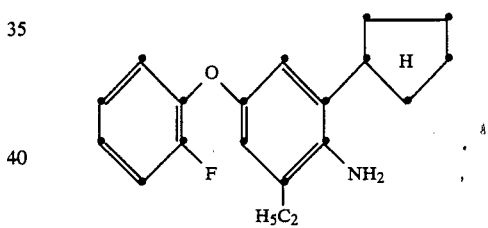,
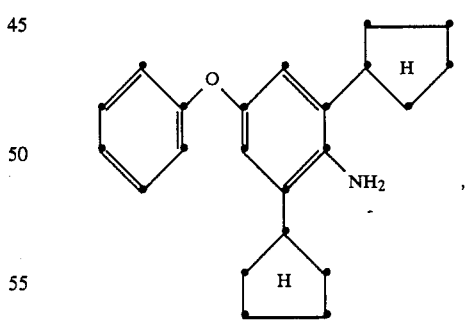,
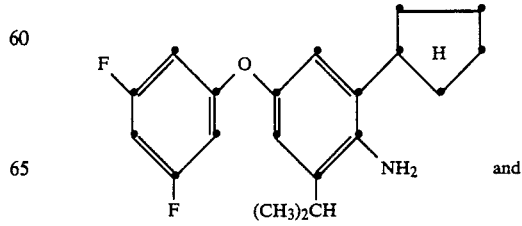 and

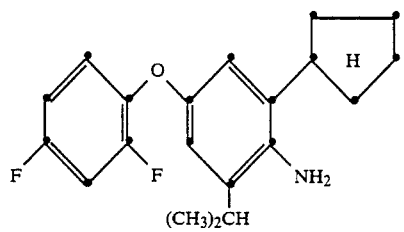

13. A compound of formula II

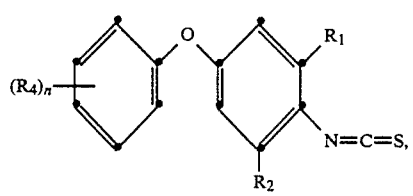

wherein
$R_1$ is $C_3$-$C_7$cycloalkyl or $C_5$-$C_6$cycloalkenyl,
$R_2$ is $C_1$-$C_4$alkyl or $C_5$-$C_6$cycloalkyl
$R_4$ is hydrogen, halogen, $C_1$-$C_4$alkyl, $C_1$-$C_3$alkoxy or $CF_3$,
n is an integer from 1 to 3.

14. A compound of formula II according to claim 13, wherein $R_1$ is $C_3$-$C_7$cycloalkyl, $R_2$ is $C_1$-$C_4$alkyl, $R_4$ is hydrogen, halogen or $C_1$-$C_3$alkyl, n is 1 or 2.

15. A compound of formula II according to claim 14, wherein $R_1$ is $C_5$-$C_6$cycloalkyl, $R_2$ is ethyl or isopropyl, $R_4$ is hydrogen or fluorine, n is 1 or 2.

16. The compound to claim 14 of formula

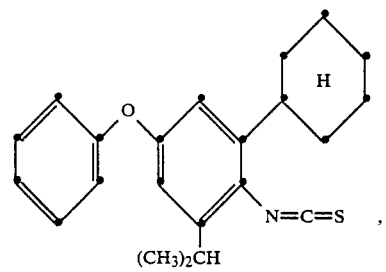

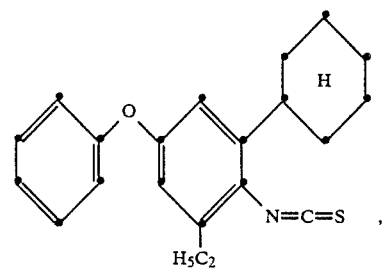

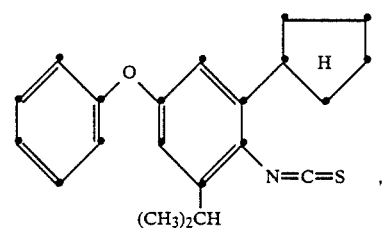

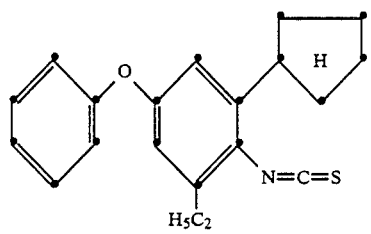

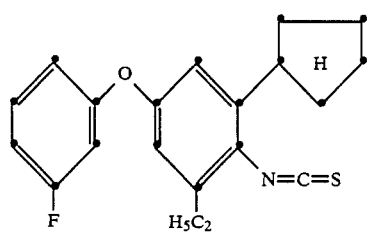

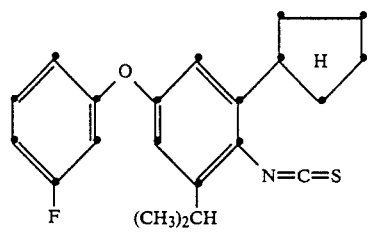

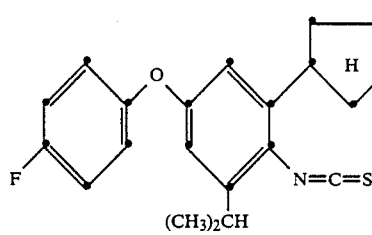

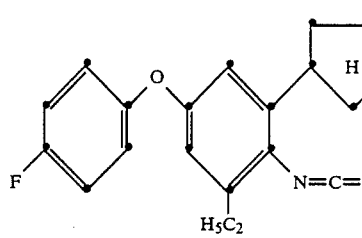

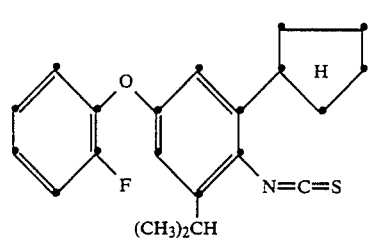

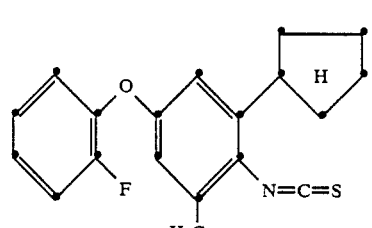

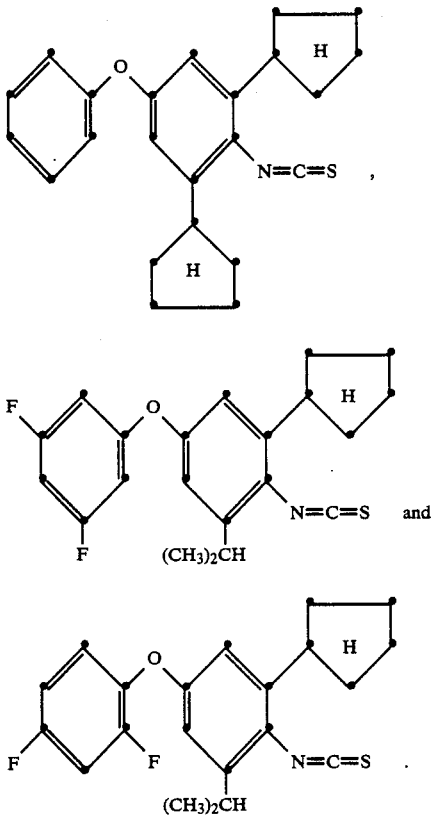

17. A pesticidal composition which contains, as active component, at least one compound of formula I

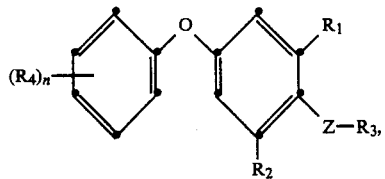

wherein
$R_1$ is $C_3$-$C_7$cycloalkyl or $C_5$-$C_6$cycloalkenyl,
$R_2$ is $C_1$-$C_6$alkyl, $C_5$-$C_6$cycloalkyl or $C_5$-$C_6$cycloalkenyl,
$R_3$ is $C_1$-$C_8$alkyl, $C_3$-$C_6$cycloalkyl, 1-cyclopropylethyl or $C_3$-$C_5$alkenyl,
$R_4$ is hydrogen, $C_3$-$C_4$alkyl, $C_1$-$C_3$alkoxy or $CF_3$,
n is an integer from 1 to 3,
Z is —NH—CS—NH—, —N=C($SR_5$)—NH— or —N=C=N—, and
$R_5$ is $C_1$-$C_5$alkyl or allyl,
or a salt thereof with an organic or inorganic acid, together with suitable carriers and/or adjuvants.

18. A pesticidal composition according to claim 17 which contains as active component at least one compound of formula I, wherein $R_1$ is $C_3$-$C_7$cycloalkyl, $R_2$ is $C_1$-$C_4$alkyl or cyclopentyl, $R_3$ is $C_1$-$C_4$alkyl or $C_3$-$C_5$cycloalkyl, $R_4$ is hydrogen, halogen or $C_1$-$C_3$alkyl, n is 1 or 2, Z is —NH—CS—NH—, —N=C($SR_5$)—NH— or —N=C=N—, and $R_5$ is $C_1$-$C_3$alkyl.

19. A pesticidal composition according to claim 18 which contains as active component at least one compound of formula I, wherein $R_1$ is $C_5$-$C_6$cycloalkyl, $R_2$ is ethyl or isopropyl, $R_3$ is isopropyl, tert-butyl or cyclopentyl, $R_4$ is hydrogen or fluorine, n is 1 or 2, and Z is —NH—CS—NH—.

20. A pesticidal composition according to claim 18 which contains as active component at least one compound of formula I, wherein $R_1$ is $C_5$-$C_6$cycloalkyl, $R_2$ is ethyl or isopropyl, $R_3$ is isopropyl, tert-butyl or cyclopentyl, $R_4$ is hydrogen or fluorine, n is 1 or 2, Z is —N=C($SR_5$)—NH—, and $R_5$ is methyl or ethyl.

21. A pesticidal composition according to claim 18 which contains as active component at least one compound of formula I, wherein $R_1$ is $C_5$-$C_6$cycloalkyl, $R_2$ is ethyl or isopropyl, $R_3$ is isopropyl, tert-butyl or cyclopentyl, $R_4$ is hydrogen or fluorine, n is 1 or 2, and Z is —N=C=N—.

22. A method of controlling pests of animals and plants, which comprises contacting said pests in their different development stages with a compound of formula I

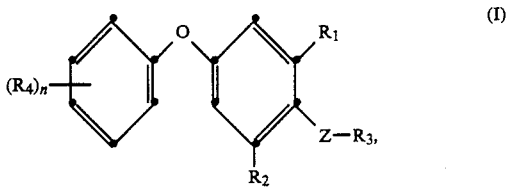

wherein
$R_1$ is $C_3$-$C_7$cycloalkyl or $C_5$-$C_6$cycloalkenyl,
$R_2$ is $C_1$-$C_8$alkyl, $C_5$-$C_6$cycloalkyl or $C_5$-$C_6$cycloalkenyl,
$R_3$ is $C_1$-$C_8$alkyl, $C_3$-$C_6$cycloalkyl, 1-cyclopropylethyl or $C_3$-$C_5$alkenyl,
$R_4$ is hydrogen, halogen, $C_1$-$C_4$alkyl, $C_1$-$C_3$alkoxy or $CF_3$,
n is an integer from 1 to 3,
Z is —NH—CS—NH—, —N=C($SR_5$)—NH— or —N=C=N—, and
$R_5$ is $C_1$-$C_5$alkyl or allyl,
or with a salt thereof with an organic or inorganic acid.

* * * * *